(12) United States Patent
Baril et al.

(10) Patent No.: US 12,419,648 B2
(45) Date of Patent: Sep. 23, 2025

(54) TWO-PART FASTENERS FOR SURGICAL CLIP APPLIERS AND SURGICAL CLIP APPLIERS FOR DEPLOYING THE SAME

(71) Applicant: Covidien LP, Mansfield, MA (US)

(72) Inventors: Jacob C. Baril, Norwalk, CT (US); Saumya Banerjee, Southington, CT (US); Garrett P. Ebersole, Hamden, CT (US)

(73) Assignee: Covidien LP, Mansfield, MA (US)

( * ) Notice: Subject to any disclaimer, the term of this patent is extended or adjusted under 35 U.S.C. 154(b) by 344 days.

(21) Appl. No.: 17/952,776

(22) Filed: Sep. 26, 2022

(65) Prior Publication Data
US 2024/0099724 A1 Mar. 28, 2024

(51) Int. Cl.
*A61B 17/128* (2006.01)
*A61B 17/00* (2006.01)
*A61B 34/30* (2016.01)

(52) U.S. Cl.
CPC ...... *A61B 17/1285* (2013.01); *A61B 2017/00407* (2013.01); *A61B 2034/302* (2016.02)

(58) Field of Classification Search
CPC .............. A61B 17/1285; A61B 17/122; A61B 17/0682; A61B 17/0643; A61B 17/064
See application file for complete search history.

(56) References Cited

U.S. PATENT DOCUMENTS

| | | |
|---|---|---|
| 3,363,628 A | 1/1968 | Wood |
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,402,445 A | 9/1983 | Green |
| 4,408,603 A | 10/1983 | Blake, III et al. |
| 4,412,539 A | 11/1983 | Jarvik |
| 4,418,694 A | 12/1983 | Beroff et al. |

(Continued)

FOREIGN PATENT DOCUMENTS

| | | |
|---|---|---|
| AU | 2013254887 A1 | 11/2013 |
| CA | 905790 A | 7/1972 |

(Continued)

OTHER PUBLICATIONS

European Search Report dated Feb. 15, 2024, issued in corresponding EP Appln. No. 23199359, 10 pages.

(Continued)

*Primary Examiner* — Brooke Labranche
(74) *Attorney, Agent, or Firm* — Draft Masters IP, LLC

(57) ABSTRACT

A surgical clip applier includes an elongated portion, a drive shaft, and an end effector. The drive shaft extends at least partially through the elongated portion. The end effector is disposed adjacent a distal end of the elongated portion, and includes a collar and a distal housing. The collar is coupled to the drive shaft and is movable relative to the distal housing. The collar is configured to support a base of a two-part fastener. The distal housing includes a leg and a C-shaped portion extending from a distal end of the leg. The C-shaped portion is configured to support a clip of the two-part fastener.

18 Claims, 13 Drawing Sheets

(56) References Cited

U.S. PATENT DOCUMENTS

| | | |
|---|---|---|
| 4,471,780 A | 9/1984 | Menges et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Yon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knopfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |

(56) References Cited

U.S. PATENT DOCUMENTS

| | | |
|---|---|---|
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,373 A | 8/1997 | Green et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |

(56) References Cited

U.S. PATENT DOCUMENTS

| | | |
|---|---|---|
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,733,514 B2 | 5/2004 | Miser |
| 6,743,240 B2 | 6/2004 | Smith et al. |
| 6,743,241 B2 | 6/2004 | Kerr |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,821,285 B2 | 11/2004 | Laufer et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,676 B2 | 5/2005 | Zubok et al. |
| 6,896,682 B1 | 5/2005 | McClellan et al. |
| 6,896,684 B2 | 5/2005 | Monassevitch et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,916,332 B2 | 7/2005 | Adams |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,001,399 B2 | 2/2006 | Damarati |
| 7,037,315 B2 | 5/2006 | Sancoff et al. |
| 7,041,119 B2 | 5/2006 | Green |
| 7,052,504 B2 | 5/2006 | Hughett |
| 7,056,330 B2 | 6/2006 | Gayton |
| 7,070,602 B2 | 7/2006 | Smith et al. |
| 7,108,700 B2 | 9/2006 | Chan |
| 7,108,703 B2 | 9/2006 | Danitz et al. |
| 7,141,056 B2 | 11/2006 | Manetakis |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,238,191 B2 | 7/2007 | Bachmann |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,312,188 B2 | 12/2007 | Kiso |
| 7,316,693 B2 | 1/2008 | Viola |
| 7,316,696 B2 | 1/2008 | Wilson, Jr. et al. |
| 7,322,995 B2 | 1/2008 | Buckman et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,367,939 B2 | 5/2008 | Smith et al. |
| 7,407,074 B2 | 8/2008 | Ortiz et al. |
| 7,419,495 B2 | 9/2008 | Menn et al. |
| 7,422,137 B2 | 9/2008 | Manzo |
| 7,431,724 B2 | 10/2008 | Manetakis et al. |
| 7,452,327 B2 | 11/2008 | Durgin et al. |
| 7,485,124 B2 | 2/2009 | Kuhns et al. |
| 7,488,335 B2 | 2/2009 | Sgro |
| 7,510,562 B2 | 3/2009 | Lindsay |
| 7,552,853 B2 | 6/2009 | Mas et al. |
| 7,559,937 B2 | 7/2009 | de la Torre et al. |
| 7,572,266 B2 | 8/2009 | Young et al. |
| 7,578,827 B2 | 8/2009 | Gadberry et al. |
| 7,582,095 B2 | 9/2009 | Shipp et al. |
| 7,585,304 B2 | 9/2009 | Hughett |
| 7,615,058 B2 | 11/2009 | Sixto, Jr. et al. |
| 7,615,060 B2 | 11/2009 | Stokes et al. |
| 7,621,926 B2 | 11/2009 | Wixey et al. |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,247 B2 | 6/2010 | Kimura et al. |
| 7,727,248 B2 | 6/2010 | Smith et al. |
| 7,731,724 B2 | 6/2010 | Huitema et al. |
| 7,731,725 B2 | 6/2010 | Gadberry et al. |
| 7,736,388 B2 | 6/2010 | Goldfarb et al. |
| 7,740,639 B2 | 6/2010 | Hummel et al. |
| 7,740,641 B2 | 6/2010 | Huitema |
| 7,744,623 B2 | 6/2010 | Anderson |

(56) References Cited

U.S. PATENT DOCUMENTS

| | | | |
|---|---|---|---|
| 7,752,853 | B2 | 7/2010 | Singh et al. |
| 7,753,250 | B2 | 7/2010 | Clauson et al. |
| 7,766,207 | B2 | 8/2010 | Mather et al. |
| 7,766,925 | B2 | 8/2010 | Stokes et al. |
| 7,770,773 | B2 | 8/2010 | Whitman et al. |
| 7,776,058 | B2 | 8/2010 | Rosenberg et al. |
| 7,780,688 | B2 | 8/2010 | Sakakine et al. |
| 7,793,813 | B2 | 9/2010 | Bettuchi |
| 7,806,903 | B2 | 10/2010 | Shibata et al. |
| 7,819,886 | B2 | 10/2010 | Whitfield et al. |
| 7,823,592 | B2 | 11/2010 | Bettuchi et al. |
| 7,857,828 | B2 | 12/2010 | Jabba et al. |
| 7,871,416 | B2 | 1/2011 | Phillips |
| 7,875,029 | B1 | 1/2011 | Hausen |
| 7,887,553 | B2 | 2/2011 | Lehman et al. |
| 7,887,554 | B2 | 2/2011 | Stokes et al. |
| 7,892,244 | B2 | 2/2011 | Monassevitch et al. |
| 7,896,895 | B2 | 3/2011 | Boudreaux et al. |
| 7,901,420 | B2 | 3/2011 | Dunn |
| 7,905,890 | B2 | 3/2011 | Whitfield et al. |
| 7,914,544 | B2 | 3/2011 | Nguyen et al. |
| 7,914,551 | B2 | 3/2011 | Ortiz et al. |
| 7,942,890 | B2 | 5/2011 | D'Agostino et al. |
| 7,947,052 | B2 | 5/2011 | Baxter, III et al. |
| 7,954,682 | B2 | 6/2011 | Giordano et al. |
| 7,963,433 | B2 | 6/2011 | Whitman et al. |
| 7,967,831 | B2 | 6/2011 | Rosenberg et al. |
| 7,988,027 | B2 | 8/2011 | Olson et al. |
| 7,998,155 | B2 | 8/2011 | Manzo |
| 8,011,550 | B2 | 9/2011 | Aranyi et al. |
| 8,011,555 | B2 | 9/2011 | Tarinelli et al. |
| 8,016,178 | B2 | 9/2011 | Olson et al. |
| 8,021,375 | B2 | 9/2011 | Aldrich et al. |
| 8,021,378 | B2 | 9/2011 | Sixto, Jr. et al. |
| 8,038,686 | B2 | 10/2011 | Huitema et al. |
| 8,048,088 | B2 | 11/2011 | Green et al. |
| 8,056,565 | B2 | 11/2011 | Zergiebel |
| 8,062,310 | B2 | 11/2011 | Shibata et al. |
| 8,062,311 | B2 | 11/2011 | Litscher et al. |
| 8,062,314 | B2 | 11/2011 | Sixto, Jr. et al. |
| 8,066,720 | B2 | 11/2011 | Knodel et al. |
| 8,066,721 | B2 | 11/2011 | Kortenbach et al. |
| 8,066,722 | B2 | 11/2011 | Miyagi et al. |
| 8,070,760 | B2 | 12/2011 | Fujita |
| 8,074,857 | B2 | 12/2011 | Peterson et al. |
| 8,075,571 | B2 | 12/2011 | Vitali et al. |
| 8,080,021 | B2 | 12/2011 | Griego |
| 8,083,668 | B2 | 12/2011 | Durgin et al. |
| 8,088,061 | B2 | 1/2012 | Wells et al. |
| 8,091,755 | B2 | 1/2012 | Kayan et al. |
| 8,100,926 | B1 | 1/2012 | Filshie et al. |
| 8,128,643 | B2 | 3/2012 | Aranyi et al. |
| 8,133,240 | B2 | 3/2012 | Damarati |
| 8,137,368 | B2 | 3/2012 | Kayan et al. |
| 8,142,451 | B2 | 3/2012 | Boulnois et al. |
| 8,157,145 | B2 | 4/2012 | Shelton, IV et al. |
| 8,157,149 | B2 | 4/2012 | Olson et al. |
| 8,157,151 | B2 | 4/2012 | Ingmanson et al. |
| 8,172,859 | B2 | 5/2012 | Matsuno et al. |
| 8,172,870 | B2 | 5/2012 | Shipp |
| 8,177,797 | B2 | 5/2012 | Shimoji et al. |
| 8,182,529 | B2 | 5/2012 | Gordon et al. |
| 8,187,290 | B2 | 5/2012 | Buckman et al. |
| 8,192,449 | B2 | 6/2012 | Maier et al. |
| 8,211,119 | B2 | 7/2012 | Palmer et al. |
| 8,211,120 | B2 | 7/2012 | Itoh |
| 8,211,124 | B2 | 7/2012 | Ainsworth et al. |
| 8,216,255 | B2 | 7/2012 | Smith et al. |
| 8,216,257 | B2 | 7/2012 | Huitema et al. |
| 8,236,012 | B2 | 8/2012 | Molitor et al. |
| 8,241,322 | B2 | 8/2012 | Whitman et al. |
| 8,246,634 | B2 | 8/2012 | Huitema et al. |
| 8,246,635 | B2 | 8/2012 | Huitema |
| 8,262,678 | B2 | 9/2012 | Matsuoka et al. |
| 8,262,679 | B2 | 9/2012 | Nguyen |
| 8,267,944 | B2 | 9/2012 | Sorrentino et al. |
| 8,267,945 | B2 | 9/2012 | Nguyen et al. |
| 8,267,946 | B2 | 9/2012 | Whitfield et al. |
| 8,272,554 | B2 | 9/2012 | Whitman et al. |
| 8,282,655 | B2 | 10/2012 | Whitfield et al. |
| 8,287,559 | B2 | 10/2012 | Barker et al. |
| 8,308,743 | B2 | 11/2012 | Matsuno et al. |
| 8,313,497 | B2 | 11/2012 | Walberg et al. |
| 8,328,822 | B2 | 12/2012 | Huitema et al. |
| 8,336,556 | B2 | 12/2012 | Zergiebel |
| 8,348,130 | B2 | 1/2013 | Shah et al. |
| 8,357,171 | B2 | 1/2013 | Whitfield et al. |
| 8,366,709 | B2 | 2/2013 | Schechter et al. |
| 8,366,726 | B2 | 2/2013 | Dennis |
| 8,371,491 | B2 | 2/2013 | Huitema et al. |
| 8,372,095 | B2 | 2/2013 | Viola |
| 8,382,773 | B2 | 2/2013 | Whitfield et al. |
| 8,398,655 | B2 | 3/2013 | Cheng et al. |
| 8,403,138 | B2 | 3/2013 | Weisshaupt et al. |
| 8,403,945 | B2 | 3/2013 | Whitfield et al. |
| 8,403,946 | B2 | 3/2013 | Whitfield et al. |
| 8,408,442 | B2 | 4/2013 | Racenet et al. |
| 8,409,222 | B2 | 4/2013 | Whitfield et al. |
| 8,409,223 | B2 | 4/2013 | Sorrentino et al. |
| 8,419,752 | B2 | 4/2013 | Sorrentino et al. |
| 8,430,892 | B2 | 4/2013 | Bindra et al. |
| 8,444,660 | B2 | 5/2013 | Adams et al. |
| 8,465,460 | B2 | 6/2013 | Yodfat et al. |
| 8,465,502 | B2 | 6/2013 | Zergiebel |
| 8,475,473 | B2 | 7/2013 | Vandenbroek et al. |
| 8,480,688 | B2 | 7/2013 | Boulnois et al. |
| 8,486,091 | B2 | 7/2013 | Sorrentino et al. |
| 8,491,608 | B2 | 7/2013 | Sorrentino et al. |
| 8,496,673 | B2 | 7/2013 | Nguyen et al. |
| 8,506,580 | B2 | 8/2013 | Zergiebel et al. |
| 8,512,357 | B2 | 8/2013 | Viola |
| 8,518,055 | B1 | 8/2013 | Cardinale et al. |
| 8,523,882 | B2 | 9/2013 | Huitema et al. |
| 8,529,585 | B2 | 9/2013 | Jacobs et al. |
| 8,529,586 | B2 | 9/2013 | Rosenberg et al. |
| 8,529,588 | B2 | 9/2013 | Ahlberg et al. |
| 8,545,486 | B2 | 10/2013 | Malkowski |
| 8,545,519 | B2 | 10/2013 | Aguirre et al. |
| 8,556,920 | B2 | 10/2013 | Huitema et al. |
| 8,568,430 | B2 | 10/2013 | Shipp |
| 8,579,918 | B2 | 11/2013 | Whitfield et al. |
| 8,585,716 | B2 | 11/2013 | Roskopf et al. |
| 8,585,717 | B2 | 11/2013 | Sorrentino et al. |
| 8,603,109 | B2 | 12/2013 | Aranyi et al. |
| 8,623,044 | B2 | 1/2014 | Timm et al. |
| 8,628,547 | B2 | 1/2014 | Weller et al. |
| 8,632,520 | B2 | 1/2014 | Otley |
| 8,636,191 | B2 | 1/2014 | Meagher |
| 8,652,151 | B2 | 2/2014 | Lehman et al. |
| 8,652,152 | B2 | 2/2014 | Aranyi et al. |
| 8,663,247 | B2 | 3/2014 | Menn et al. |
| 8,685,048 | B2 | 4/2014 | Adams et al. |
| 8,690,899 | B2 | 4/2014 | Kogiso et al. |
| 8,708,210 | B2 | 4/2014 | Zemlok et al. |
| 8,708,213 | B2 | 4/2014 | Shelton, IV et al. |
| 8,709,027 | B2 | 4/2014 | Adams et al. |
| 8,715,299 | B2 | 5/2014 | Menn et al. |
| 8,720,766 | B2 | 5/2014 | Hess et al. |
| 8,734,469 | B2 | 5/2014 | Pribanic et al. |
| 8,747,423 | B2 | 6/2014 | Whitfield et al. |
| 8,753,356 | B2 | 6/2014 | Vitali et al. |
| 8,758,392 | B2 | 6/2014 | Crainich |
| 8,771,169 | B2 | 7/2014 | Whitman et al. |
| 8,795,302 | B2 | 8/2014 | Wild |
| 8,808,310 | B2 | 8/2014 | Jones et al. |
| 8,814,884 | B2 | 8/2014 | Whitfield et al. |
| 8,821,516 | B2 | 9/2014 | Huitema |
| 8,828,023 | B2 | 9/2014 | Neff et al. |
| 8,839,954 | B2 | 9/2014 | Disch |
| 8,845,659 | B2 | 9/2014 | Whitfield et al. |
| 8,894,665 | B2 | 11/2014 | Sorrentino et al. |
| 8,894,666 | B2 | 11/2014 | Schulz et al. |
| 8,900,253 | B2 | 12/2014 | Aranyi et al. |
| 8,915,930 | B2 | 12/2014 | Huitema et al. |

(56) References Cited

U.S. PATENT DOCUMENTS

| | | |
|---|---|---|
| 8,915,931 B2 | 12/2014 | Boudreaux et al. |
| 8,939,974 B2 | 1/2015 | Boudreaux et al. |
| 8,945,151 B2 | 2/2015 | Salas |
| 8,950,646 B2 | 2/2015 | Viola |
| 8,968,337 B2 | 3/2015 | Whitfield et al. |
| 8,968,342 B2 | 3/2015 | Wingardner, III et al. |
| 8,973,804 B2 | 3/2015 | Hess et al. |
| 8,986,343 B2 | 3/2015 | Bourque et al. |
| 8,998,935 B2 | 4/2015 | Hart |
| 9,011,464 B2 | 4/2015 | Zammataro |
| 9,011,465 B2 | 4/2015 | Whitfield et al. |
| 9,028,511 B2 | 5/2015 | Weller et al. |
| 9,060,779 B2 | 6/2015 | Martinez |
| 9,084,604 B2 | 7/2015 | Litscher et al. |
| 9,089,334 B2 | 7/2015 | Sorrentino et al. |
| 9,113,892 B2 | 8/2015 | Malkowski et al. |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,226,825 B2 | 1/2016 | Starksen et al. |
| 9,232,947 B2 | 1/2016 | Brenner et al. |
| 9,265,486 B2 | 2/2016 | Hughett, Sr. et al. |
| 9,271,737 B2 | 3/2016 | Castro et al. |
| 9,282,972 B1 | 3/2016 | Patel et al. |
| 9,282,973 B2 | 3/2016 | Hughett, Sr. et al. |
| 9,358,011 B2 | 6/2016 | Sorrentino et al. |
| 9,364,216 B2 | 6/2016 | Rockrohr et al. |
| 9,364,240 B2 | 6/2016 | Whitfield et al. |
| 9,370,400 B2 | 6/2016 | Parihar |
| 9,393,024 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,433,422 B2 | 9/2016 | Crainich et al. |
| 9,439,654 B2 | 9/2016 | Sorrentino et al. |
| 9,445,810 B2 | 9/2016 | Cappola |
| 9,445,820 B2 | 9/2016 | Whiting |
| 9,456,824 B2 | 10/2016 | Willett et al. |
| 9,468,444 B2 | 10/2016 | Menn et al. |
| 9,480,477 B2 | 11/2016 | Aranyi et al. |
| 9,480,480 B2 | 11/2016 | Santilli et al. |
| 9,486,225 B2 | 11/2016 | Michler et al. |
| 9,498,227 B2 | 11/2016 | Zergiebel et al. |
| 9,504,472 B2 | 11/2016 | Kamler |
| 9,517,064 B2 | 12/2016 | Sarradon |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,561,038 B2 | 2/2017 | Shelton, IV et al. |
| 9,566,066 B2 | 2/2017 | Kasvikis |
| 9,597,089 B2 | 3/2017 | Menn |
| 9,642,627 B2 | 5/2017 | Zammataro |
| 9,681,877 B2 | 6/2017 | Blake, III et al. |
| 9,687,247 B2 | 6/2017 | Aranyi et al. |
| 9,700,324 B2 | 7/2017 | Mazzucco et al. |
| 9,717,504 B2 | 8/2017 | Huitema |
| 9,717,505 B2 | 8/2017 | Whitfield et al. |
| 9,724,163 B2 | 8/2017 | Orban |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,763,669 B2 | 9/2017 | Griego |
| 9,775,623 B2 | 10/2017 | Zammataro et al. |
| 9,775,624 B2 | 10/2017 | Rockrohr et al. |
| 9,782,164 B2 | 10/2017 | Mumaw et al. |
| 9,782,181 B2 | 10/2017 | Vitali et al. |
| 9,795,385 B2 | 10/2017 | Abbott et al. |
| 9,808,257 B2 | 11/2017 | Armenteros et al. |
| 9,848,886 B2 | 12/2017 | Malkowski et al. |
| 9,855,043 B2 | 1/2018 | Malkowski |
| 9,883,866 B2 | 2/2018 | Roundy et al. |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2002/0123742 A1 | 9/2002 | Baxter et al. |
| 2003/0014060 A1 | 1/2003 | Wilson et al. |
| 2003/0114867 A1 | 6/2003 | Bolduc et al. |
| 2003/0208231 A1 | 11/2003 | Williamson et al. |
| 2003/0229360 A1 | 12/2003 | Gayton |
| 2004/0097970 A1 | 5/2004 | Hughett |
| 2004/0097971 A1 | 5/2004 | Hughett |
| 2004/0133215 A1 | 7/2004 | Baxter |
| 2004/0138681 A1 | 7/2004 | Pier |
| 2004/0167545 A1 | 8/2004 | Sadler et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0010242 A1 | 1/2005 | Lindsay |
| 2005/0090837 A1 | 4/2005 | Sixto et al. |
| 2005/0096670 A1 | 5/2005 | Wellman et al. |
| 2005/0096671 A1 | 5/2005 | Wellman et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0125010 A1 | 6/2005 | Smith et al. |
| 2005/0149068 A1 | 7/2005 | Williams et al. |
| 2005/0149069 A1 | 7/2005 | Bertolero et al. |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0216036 A1 | 9/2005 | Nakao |
| 2005/0216056 A1 | 9/2005 | Valdevit et al. |
| 2005/0222665 A1 | 10/2005 | Aranyi |
| 2005/0228416 A1 | 10/2005 | Burbank et al. |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2006/0000867 A1 | 1/2006 | Shelton et al. |
| 2006/0004388 A1 | 1/2006 | Whayne et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0015144 A1 | 1/2006 | Burbank et al. |
| 2006/0020271 A1 | 1/2006 | Stewart et al. |
| 2006/0064117 A1 | 3/2006 | Aranyi et al. |
| 2006/0079115 A1 | 4/2006 | Aranyi |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0124485 A1 | 6/2006 | Kennedy |
| 2006/0163312 A1 | 7/2006 | Viola et al. |
| 2006/0173470 A1 | 8/2006 | Oray et al. |
| 2006/0190013 A1 | 8/2006 | Menn |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235439 A1 | 10/2006 | Molitor et al. |

(56) References Cited

U.S. PATENT DOCUMENTS

| | | |
|---|---|---|
| 2006/0241655 A1 | 10/2006 | Viola |
| 2006/0259045 A1 | 11/2006 | Damarati |
| 2006/0259049 A1 | 11/2006 | Harada et al. |
| 2007/0021766 A1 | 1/2007 | Belagali et al. |
| 2007/0038233 A1 | 2/2007 | Martinez et al. |
| 2007/0049947 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0083218 A1 | 4/2007 | Morris |
| 2007/0093790 A1 | 4/2007 | Downey et al. |
| 2007/0112365 A1 | 5/2007 | Hilal et al. |
| 2007/0118161 A1 | 5/2007 | Kennedy et al. |
| 2007/0118174 A1 | 5/2007 | Chu |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203510 A1 | 8/2007 | Bettuchi |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0045981 A1 | 2/2008 | Margolin et al. |
| 2008/0051808 A1 | 2/2008 | Rivera et al. |
| 2008/0103510 A1 | 5/2008 | Taylor et al. |
| 2008/0147092 A1 | 6/2008 | Rogge et al. |
| 2008/0167665 A1 | 7/2008 | Arp et al. |
| 2008/0228199 A1 | 9/2008 | Cropper et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312670 A1 | 12/2008 | Utze et al. |
| 2009/0088783 A1 | 4/2009 | Kennedy et al. |
| 2009/0182193 A1 | 7/2009 | Whitman et al. |
| 2009/0204115 A1 | 8/2009 | Dees, Jr. et al. |
| 2009/0209946 A1 | 8/2009 | Swayze et al. |
| 2009/0228023 A1 | 9/2009 | Cui |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2009/0326558 A1 | 12/2009 | Cui et al. |
| 2010/0089970 A1 | 4/2010 | Smith et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0087220 A1 | 4/2011 | Felder et al. |
| 2011/0087268 A1 | 4/2011 | Livneh |
| 2011/0144662 A1 | 6/2011 | McLawhorn et al. |
| 2011/0208211 A1 | 8/2011 | Whitfield et al. |
| 2011/0208212 A1 | 8/2011 | Zergiebel et al. |
| 2011/0218554 A1 | 9/2011 | Cheng et al. |
| 2011/0224700 A1 | 9/2011 | Schmidt et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0046671 A1 | 2/2012 | Matsuoka et al. |
| 2012/0048759 A1 | 3/2012 | Disch et al. |
| 2012/0053402 A1 | 3/2012 | Conlon et al. |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0330326 A1 | 12/2012 | Creston et al. |
| 2013/0041379 A1 | 2/2013 | Bodor et al. |
| 2013/0131697 A1 | 5/2013 | Hartoumbekis |
| 2013/0165951 A1 | 6/2013 | Blake, III |
| 2013/0172909 A1 | 7/2013 | Harris |
| 2013/0172910 A1 | 7/2013 | Malkowski |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0325057 A1 | 12/2013 | Arson et al. |
| 2014/0074143 A1 | 3/2014 | Fitzgerald et al. |
| 2014/0151432 A1 | 6/2014 | Weaver |
| 2014/0188159 A1 | 7/2014 | Steege |
| 2014/0263565 A1 | 9/2014 | Lytle, IV et al. |
| 2014/0276970 A1 | 9/2014 | Messerly et al. |
| 2014/0371728 A1 | 12/2014 | Vaughn |
| 2015/0032131 A1 | 1/2015 | Sorrentino et al. |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2016/0100835 A1 | 4/2016 | Linder et al. |
| 2016/0113655 A1 | 4/2016 | Holsten |
| 2016/0151071 A1 | 6/2016 | Tokarz et al. |
| 2016/0213377 A1 | 7/2016 | Shankarsetty |
| 2016/0242767 A1 | 8/2016 | Kasvikis |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Murthy Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |

(56) References Cited

U.S. PATENT DOCUMENTS

| | | |
|---|---|---|
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | | |
|---|---|---|---|
| CA | 1163889 A | | 3/1984 |
| CN | 103251441 A | | 8/2013 |
| CN | 104605911 B | | 2/2017 |
| DE | 202005001664 U1 | | 5/2005 |
| DE | 202007003398 U1 | | 6/2007 |
| EP | 0000756 A1 | | 2/1979 |
| EP | 0406724 A1 | | 1/1991 |
| EP | 0514139 A2 | | 11/1992 |
| EP | 0732078 A2 | | 9/1996 |
| EP | 1769757 A1 | | 4/2007 |
| EP | 3132756 A1 | | 2/2017 |
| GB | 2044108 A | | 10/1980 |
| GB | 2073022 A | | 10/1981 |
| JP | 2003033361 A | | 2/2003 |
| JP | 2006154230 A | | 6/2006 |
| JP | 2006277221 A | | 10/2006 |
| JP | 2008017876 A | | 1/2008 |
| JP | 2011186812 A | | 9/2011 |
| JP | 2013166982 A | | 8/2013 |
| WO | 9003763 A1 | | 4/1990 |
| WO | 0042922 A1 | | 7/2000 |
| WO | 0166001 A2 | | 9/2001 |
| WO | 0167965 A1 | | 9/2001 |
| WO | 2016192096 A1 | | 12/2016 |
| WO | 2016192718 A2 | | 12/2016 |
| WO | 2016197350 A1 | | 12/2016 |
| WO | 2016206015 A1 | | 12/2016 |
| WO | 2017084000 A1 | | 5/2017 |
| WO | 2017146138 A1 | | 8/2017 |

OTHER PUBLICATIONS

EP Patent Application No. 23 199 359.03-1122, Office Action mailed Jul. 21, 2025, 8pgs.

TWO-PART FASTENERS FOR SURGICAL CLIP APPLIERS AND SURGICAL CLIP APPLIERS FOR DEPLOYING THE SAME

BACKGROUND

This disclosure relates to surgical instruments and to fasteners for use with surgical instruments. More particularly, this disclosure relates to two-part surgical clips and surgical clip appliers for deploying the same.

Surgical clip appliers are known in the art and are used for a number of distinct and useful surgical procedures including endoscopic, open, and robotic surgical procedures. Surgical clip appliers having various sizes (e.g., diameters) are configured to apply a variety of diverse surgical clips, and are capable of applying a single or multiple surgical clips within the body cavity. Such surgical clips are typically fabricated from a biocompatible material and are usually compressed over tissue. Once applied to tissue, the compressed surgical clip terminates the flow of fluid through the tissue.

Certain surgical procedures or situations may benefit from the implementation of a partially-formed surgical clip to crimp a vessel, or to retain a catheter in a vessel without occluding the vessel (e.g., during cholangiograms), for instance.

SUMMARY

This disclosure relates to a surgical clip applier including an elongated portion, a drive shaft, and an end effector. The elongated portion defines a longitudinal axis and includes a distal end. The drive shaft extends at least partially through the elongated portion. The end effector is disposed adjacent the distal end of the elongated portion, and includes a collar and a distal housing. The collar is coupled to the drive shaft and is movable relative to the distal housing. The collar is configured to support a base of a two-part fastener. The distal housing includes a leg and a C-shaped portion extending from a distal end of the leg. The C-shaped portion of the distal housing is configured to support a clip of the two-part fastener.

In disclosed embodiments, a distal-most end of the C-shaped portion of the distal housing defines an aperture. In embodiments, the C-shaped portion of the distal housing defines a slot extending laterally from the aperture. The slot is configured to support a portion of the clip of the two-part fastener.

In disclosed embodiments, the distal housing is fixed from longitudinal movement relative to the elongated portion.

In disclosed embodiments, the collar of the end effector defines a recess for accepting the base of the two-part fastener partially in the recess.

In disclosed embodiments, the collar of the end effector defines a first leg aperture and a second leg aperture. The first leg aperture is configured to allow a first leg of the clip of the two-part fastener to extend through the collar. The second leg aperture is configured to allow a second leg of the clip of the two-part fastener to extend through the collar. In embodiments, the first leg aperture and the second leg aperture are defined within a recess of the collar.

This disclosure also relates to a surgical clip-applying system including a surgical clip applier and a two-part fastener. The surgical clip applier includes an elongated portion defining a longitudinal axis and including a distal end. The end effector is disposed adjacent the distal end of the elongated portion, and includes a collar and a distal housing. At least one of the collar or the distal housing is movable along the longitudinal axis relative to the elongated portion. The two-part fastener includes a base and a clip. The base is configured to be supported by the collar of the end effector of the surgical clip applier. The clip is configured to be supported by the distal housing of the end effector of the surgical clip applier, and includes a first leg and a second leg. A predetermined amount movement of at least one of the collar or the distal housing relative to the elongated portion causes the base of the two-part fastener to engage the clip of the two-part fastener.

In disclosed embodiments, the distal housing of the end effector includes a C-shaped portion.

In disclosed embodiments, the base of the two-part fastener defines a first aperture and a second aperture. In embodiments, the clip of the two-part fastener is C-shaped and includes a first leg and a second leg. The first leg is configured to selectively extend through the first aperture of the base of the two-part fastener, and the second leg configured to selectively extend through the second aperture of the base of the two-part fastener. In embodiments, each of the first leg and the second leg of the clip of the two-part fastener includes a plurality of teeth configured to engage the base of the two-part fastener in a ratcheting manner.

In disclosed embodiments, a distal-most end of the distal housing of the end effector defines an aperture. In embodiments, a distal end of the clip of the two-part fastener includes a distal tip configured to selectively extend through the aperture of the distal housing of the end effector. In embodiments, the distal tip of the clip of the two-part fastener defines a slit extending generally parallel to the first leg of the clip of the two-part fastener. In embodiments, when the distal tip of the clip of the two-part fastener is extended through the aperture of the distal housing of the end effector, the slit of the distal tip extends distally beyond the distal-most end of the distal housing of the end effector.

In disclosed embodiments, the base of the two-part fastener is supported partially within a recess of the collar of the end effector.

In disclosed embodiments, the collar of the end effector defines a first aperture and a second aperture, and the base of the two-part fastener defines a first aperture and a second aperture. In embodiments, after a predetermined amount of movement of the at least one of the collar or the distal housing relative to the elongated portion, the first leg of the clip of the two-part fastener extends through the first aperture of the collar and through the first aperture of the base of the two-part fastener, and the second leg of the clip of the two-part fastener extends through the second aperture of the collar and through the second aperture of the base of the two-part fastener.

This disclosure also relates to a two-part fastener for use with a surgical clip applier. The two-part fastener includes a base and a clip. The base includes a rectangular portion, a first aperture extending through the rectangular portion, and a second aperture extending through the rectangular portion. The clip includes a first leg, a second leg, and a distal tip interconnecting the first leg and the second leg. The first leg includes a plurality of teeth and is configured to selectively extend at least partially through the first aperture of the base. The second leg includes a plurality of teeth and is configured to selectively extend at least partially through the second aperture of the base.

In disclosed embodiments, the first leg of the clip is generally parallel to the second leg of the clip.

In disclosed embodiments, at least a portion of the distal tip is generally parallel to the first leg and the second leg. In embodiments, the distal tip defines a slit extending through a proximal portion of the distal tip.

In disclosed embodiments, the first leg of the base is configured to selectively extend completely through the first aperture of the base. In embodiments, the second leg of the base is configured to selectively extend completely through the second aperture of the base.

In disclosed embodiments, the base is configured to engage the clip in a plurality of discrete positions.

This disclosure additionally relates to a method of fixing a catheter to a vessel. The method includes positioning an end effector of a surgical clip applier adjacent the vessel such that a distal housing of the end effector is positioned distally of the vessel, and a collar of the end effector is positioned proximally of the vessel. The method also includes moving the collar of the end effector distally such that a base of a two-part fastener supported by the collar moves toward a clip of the two-part fastener supported by the distal housing of the end effector. The method also includes moving the collar of the end effector distally such that a first aperture of the base of the two-part fastener engages a first leg of the clip of the two-part fastener and a second aperture of the base engages a second leg of the clip. The method also includes moving the collar of the end effector distally such that the base of the two-part fastener is in a desired discrete position relative to the clip of the two-part fastener such that the catheter is sufficiently fixed to the vessel and such that the vessel is not occluded.

In disclosed embodiments, moving the collar of the end effector distally until the base of the two-part fastener is in a desired discrete position relative to the clip of the two-part fastener includes moving the collar from a first discrete position to a second discrete position.

In disclosed embodiments, the method also includes moving the collar of the end effector distally such that the first leg of the clip of the two-part fastener extends through a first aperture of the collar, and such that the second leg of the clip of the two-part fastener extends through a second aperture of the collar.

In disclosed embodiments, the method also includes moving the collar proximally relative to the base of the two-part fastener. In embodiments, the method also includes moving the distal housing of the end effector distally relative to the clip of the two-part fastener such that a distal tip of the clip moves through an aperture of the distal housing. In embodiments, moving the distal housing of the end effector distally relative to the clip of the two-part fastener is performed after moving the collar proximally relative to the base of the two-part fastener. In embodiments, the method also includes cutting the distal tip of the clip of the two-part fastener to separate the first leg from the second leg of the clip of the two-part fastener.

BRIEF DESCRIPTION OF THE DRAWINGS

Embodiments of the disclosure are described in detail with reference to the drawing figures wherein like reference numerals identify similar or identical structural elements and.

DETAILED DESCRIPTION

Figure 1:
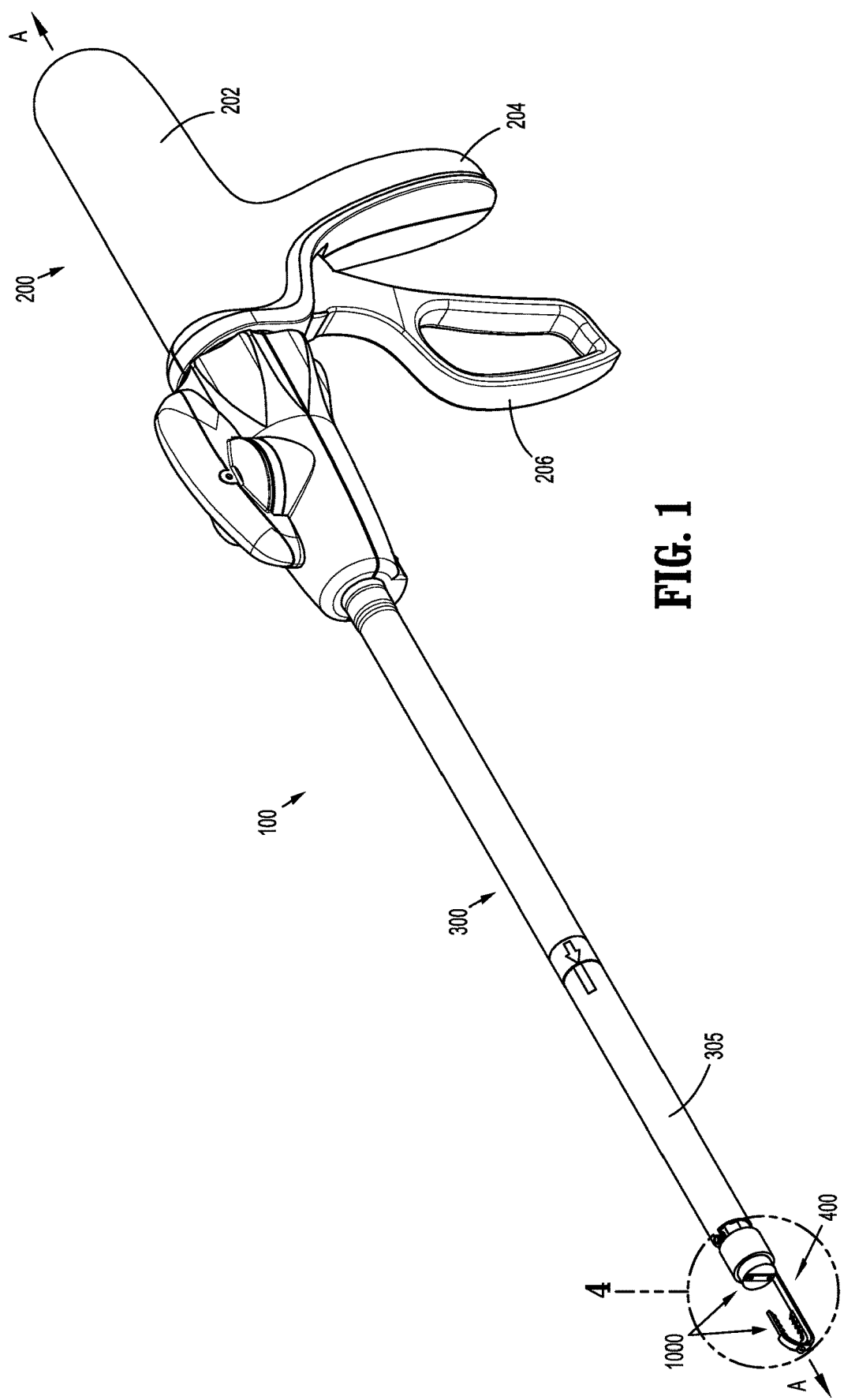
FIG. 1 is a front, perspective view of an endoscopic surgical clip applier illustrating an end effector in an open position and supporting a two-part fastener, in accordance with embodiments of the disclosure.
Figure 2:
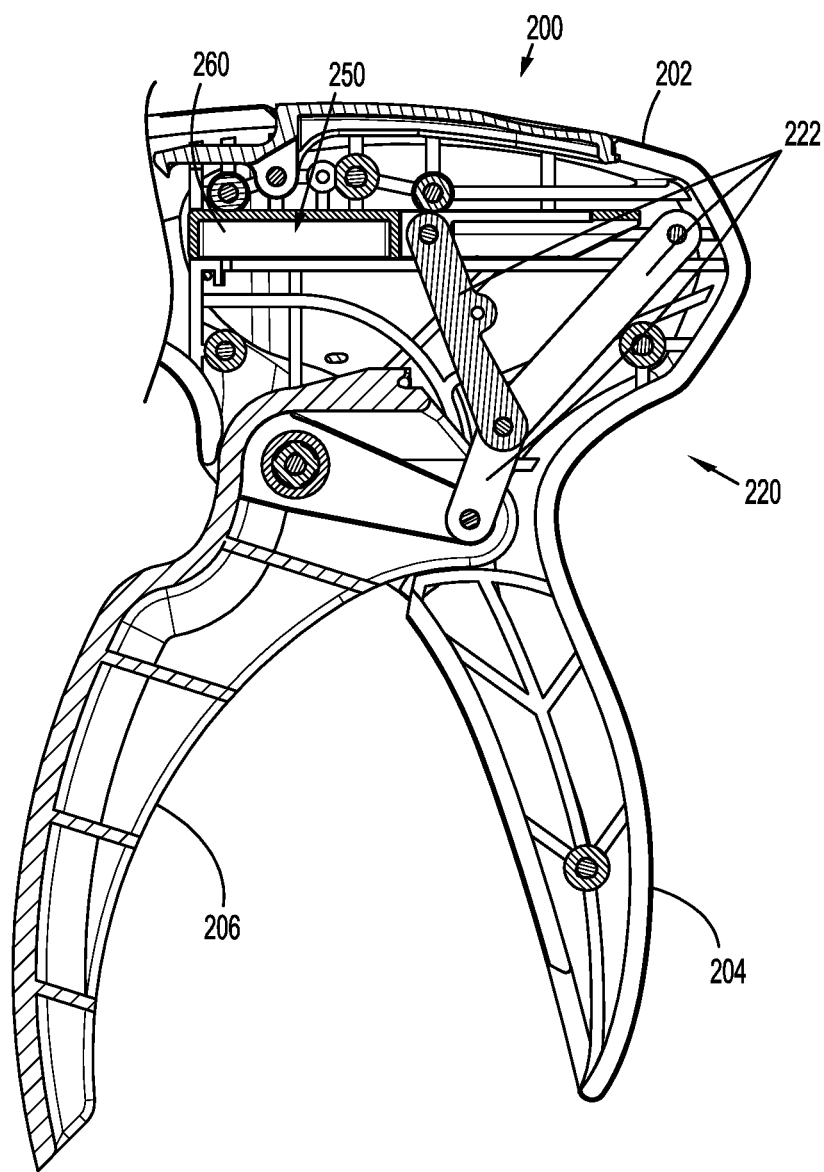
FIG. 2 is a side view of a handle assembly of the surgical clip applier of FIG. 1, with portions removed, and illustrating a trigger of the surgical clip applier disposed in an un-actuated position.
Figure 3:
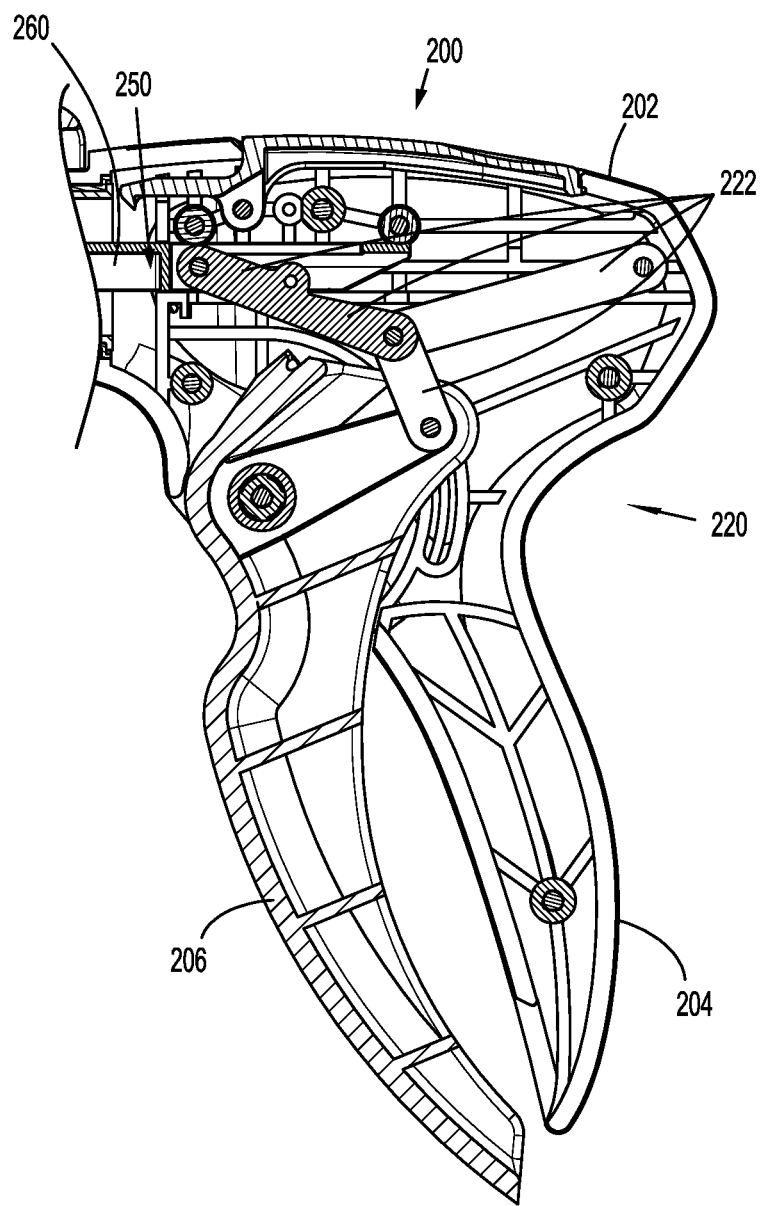
FIG. 3 is a side view of the handle assembly of the surgical clip applier of FIG. 1, with portions removed, and illustrating the trigger in an actuated position.

Embodiments of the disclosed surgical clip applier and two-part fastener are described in detail with reference to the drawings, in which like reference numerals designate identical or corresponding elements in each of the several views. Non-limiting examples of surgical clip appliers according to the disclosure include manual, robotic, mechanical and/or electromechanical, and the like. As used herein the term "distal" refers to that portion of the two-part fastener, surgical clip applier, or component thereof, farther from the user, while the term "proximal" refers to that portion of the two-part fastener, surgical clip applier, or component thereof, closer to the user.

As will be described in greater detail below, the disclosure includes a two-part fastener, and a surgical clip applier for utilizing the two-part fastener to fix a catheter to a vessel. Related methods of use are also encompassed by this disclosure.

FIGS. 1-20 illustrate surgical clip appliers and two-part fasteners in accordance with embodiments of the disclosure. While the figures illustrate an endoscopic surgical clip applier (e.g., FIG. 1), and a robotic surgical clip applier (FIG. 20), other types of surgical clip appliers (e.g., open surgical clip appliers) are encompassed by the scope of the present disclosure and are usable with the disclosed two-part fasteners. For simplicity, each of the disclosed surgical clip appliers is generally referred to as surgical clip applier 100.

With initial reference to FIG. 1, the surgical clip applier 100 includes a handle assembly 200, an endoscopic or elongated portion 300 extending distally from the handle assembly 200 and defining a longitudinal axis "A-A," and an end effector 400 disposed adjacent a distal end of the elongated portion 300. A two-part fastener 1000 is supported by the end effector 400. Additionally, an actuation assembly 220 (FIGS. 2-3) and a drive assembly 250 (FIGS. 2-3) are disposed in mechanical cooperation with the handle assembly 200 and are configured to distally advance one part of the two-part fastener 1000.

While details of a particular handle assembly 200, a particular actuation assembly 220, and a particular drive assembly 250 are discussed below, the disclosed surgical clip applier 100 is usable with other types of handle assemblies, actuation assemblies, and drive assemblies without departing from the scope of the disclosure.

Figure 4:
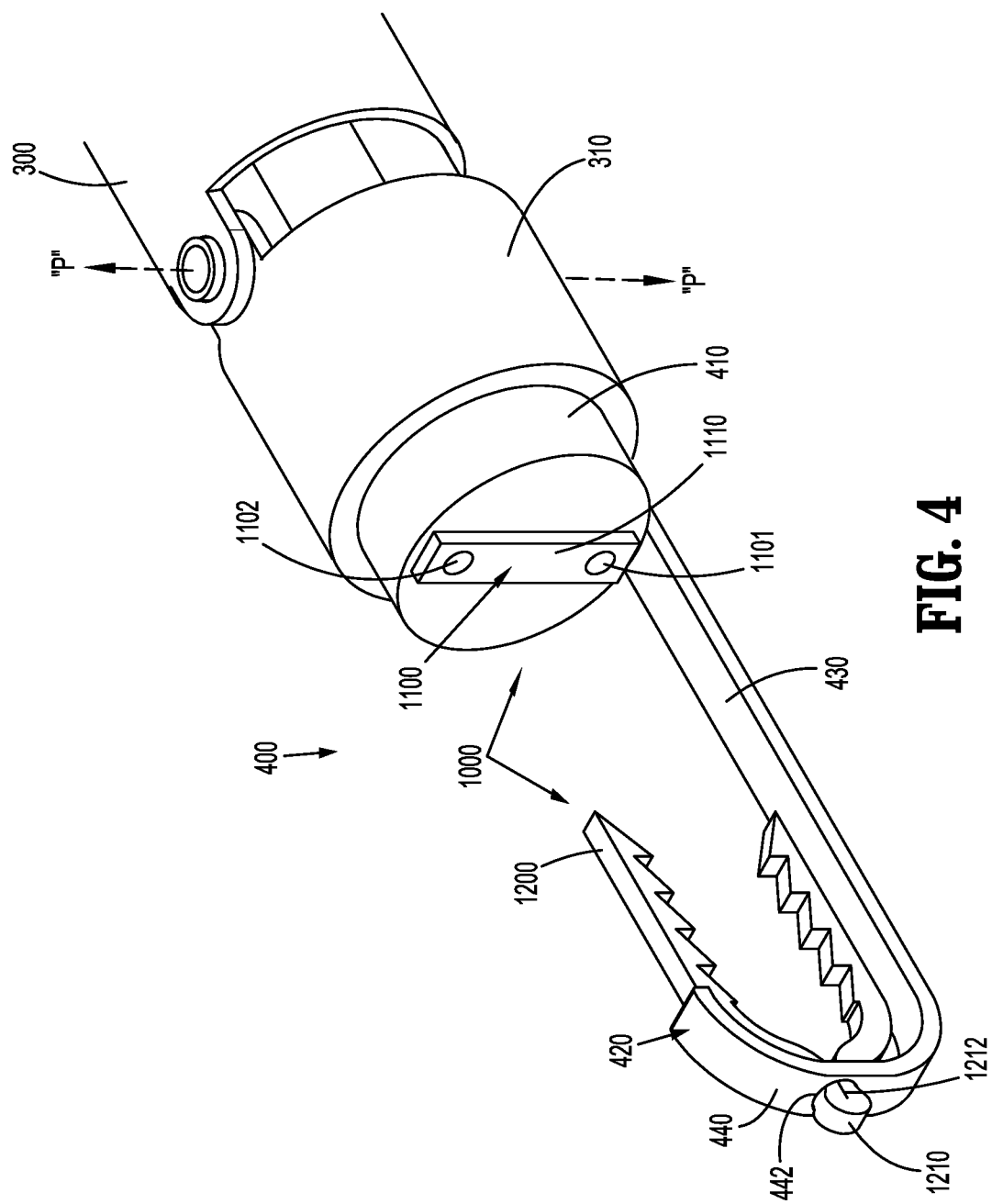
FIG. 4 is an enlarged view of the area of detail indicated in FIG. 1 illustrating a distal end of the surgical clip applier supporting the two-part fastener.
Figure 5:
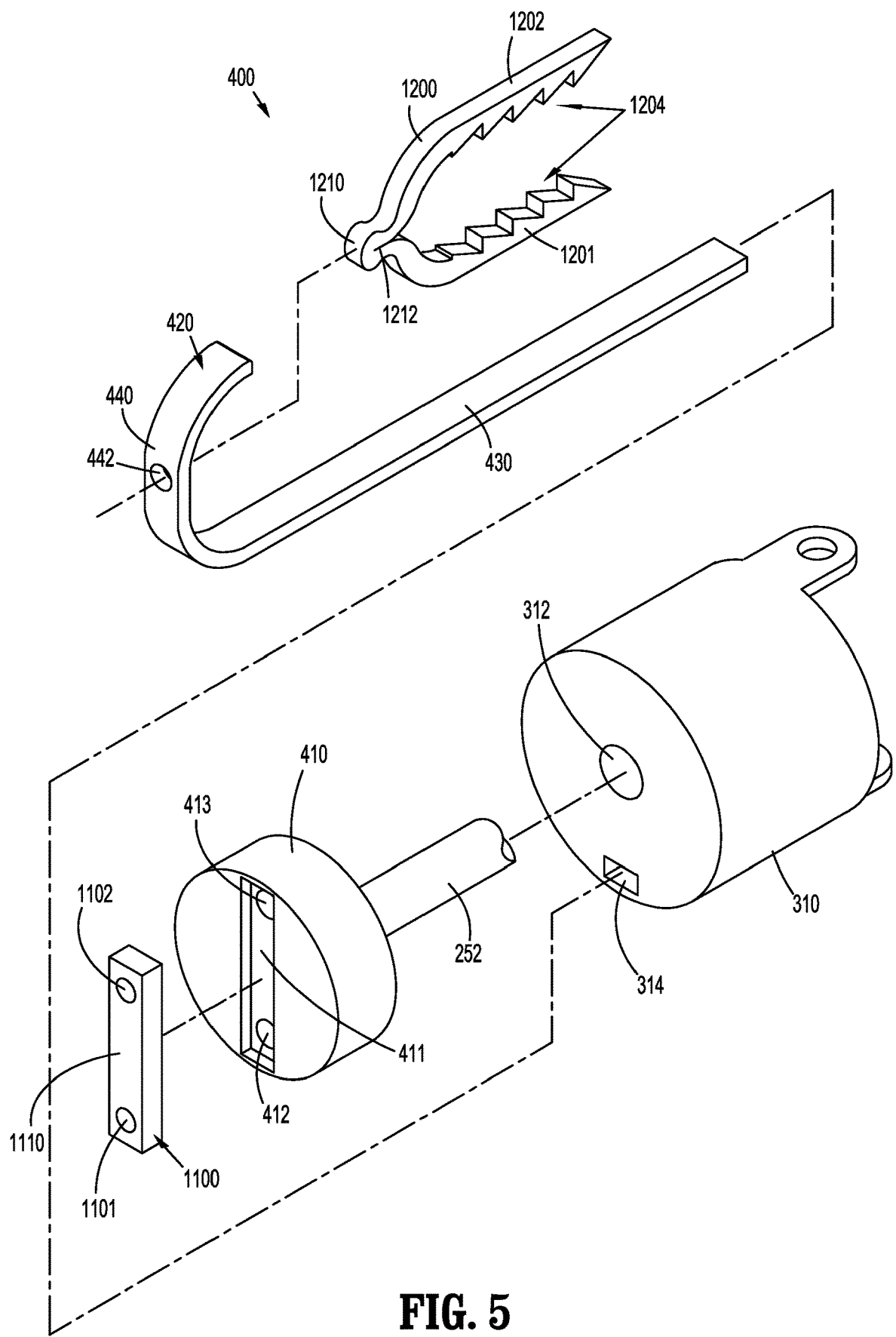
FIG. 5 is a perspective, exploded view of the distal end of the surgical clip applier and two-part fastener of FIG. 1.

Referring now to FIGS. 1-5, further details of the handle assembly 200, the actuation assembly 220, the drive assembly 250, and the distal portion of the surgical clip applier 100 are shown. The handle assembly 200 includes a handle housing 202, a stationary handle 204, and a pivotable handle 206. The actuation assembly 220 includes a plurality of linkages 222 disposed in operative engagement with the pivotable handle 206. The drive assembly 250 includes a drive shaft 252 (FIG. 5). Generally, actuation of the pivotable handle 206 causes the drive shaft 252 to move distally, which, in turn, causes formation of the two-part fastener 1000. Further details of suitable drive assemblies and actuation assemblies are described in pending U.S. patent application Ser. No. 17/572,669, filed on Jan. 11, 2022, and U.S. Pat. No. 11,246,601, the entire contents of each of which are incorporated by reference herein.

With particular reference to FIGS. 4 and 5, the end effector 400 includes a collar 410 and a distal housing 420, and the two-part fastener 1000 includes a first part or a base 1100 and a second part or a clip 1200. The collar 410 of the end effector 400 supports the base 1100, and the distal housing 420 of the end effector 400 supports the clip 1200.

With continued reference to FIG. 4, the collar 410 of the end effector 400 defines a recess 411, a first aperture or first leg aperture 412, and a second aperture or second leg aperture 413. The recess 411 is configured to releasably receive the base 1100 of the two-part fastener 1000 at least partially therein, e.g., in a press-fit manner. The first aperture 412 and the second aperture 413 are each configured to align with a respective first aperture 1101 and a second aperture 1102 of the base 1100 of the two-part fastener 1000 when the base 1100 is engaged with the recess 411. The first aperture 412 of the collar 410 is configured to allow at least a portion of a first leg 1201 of the clip 1200 to pass through the first aperture 412, and the second aperture 413 of the collar 410 is configured to allow at least a portion of a second leg 1202 of the clip 1200 to pass through the second aperture 413.

Referring now to FIGS. 4-7, the distal housing 420 of the end effector 400 generally includes a leg 430, and a C-shaped portion 440 extending from a distal end of the leg 430. A distal-most end of the C-shaped portion 440 defines an aperture 442 extending therethrough. The aperture 442 is configured to allow a distal tip 1210 of the clip 1200 of the two-part fastener 1000 to extend therethrough. The C-shaped portion 440 of the distal housing 420 also defines a slot 446 extending from the aperture 442 to a cantilevered end 450 of the distal housing 420. The slot 446 is configured to support a portion of the second leg 1202 of the clip 1200 to help stabilize the clip 1200 relative to the distal housing 420, for instance.

With reference to FIGS. 4 and 5, a pivotable member 310 is disposed at a distal end of the elongated portion 300. The pivotable member 310 is pivotable relative to an intermediate portion 305 (FIG. 1) of the elongated portion 300 about axis "P-P" in FIG. 4 to allow for articulation of the end effector 400 relative to the intermediate portion 305 of the elongated portion 300. Pivotable member 310 includes a first aperture 312 for slidingly engaging the drive shaft 252, and a second aperture 314 for fixedly engaging a proximal portion of the leg 430 of the distal housing 420 of the end effector 400.

With continued reference to FIGS. 4 and 5, a distal end of the drive shaft 252 is mechanically coupled to the collar 410, such that distal translation of the drive shaft 252 relative to the handle assembly 200 results in a corresponding distal translation of the collar 410 relative to the distal housing 420 of the end effector 400. As discussed in further detail below, sufficient distal translation of the collar 410 relative to the distal housing 420 causes the base 1100 of the two-part fastener 1000 to engage the clip 1200 of the two-part fastener 1000.

With particular reference to FIGS. 4-7, further details of the two-part fastener 1000 are described. The base 1100 of the two-part fastener 1000 is configured to engage the clip 1200 of the two-part fastener 1000 in a plurality of discrete positions. In each position of engagement, a distance "d" between the base 1100 and the distal tip 1210 of the clip 1200 is different (see FIG. 13, for instance).

The base 1100 may include a generally rectangular body portion 1110 as shown, or body portion 1110 may be of any other suitable shape. The first aperture 1101 and the second aperture 1102 extend through the body portion 1110. The clip 1200 is generally U-shaped and includes the first leg 1201, and the second leg 1202, with the distal tip 1210 interconnecting the first leg 1201 and the second leg 1202.

Each of the first leg 1201 and the second leg 1202 includes a plurality of teeth 1204 for engaging the base 1100 in a ratcheting manner. The plurality of teeth 1204 may be defined by other shapes and other angles than those shown herein without departing from the scope of the present disclosure. Additionally, the amount or number of teeth included in the plurality of teeth 1204 may be more or fewer than the amount shown in the accompanying figures without departing from the scope of the present disclosure.

Figure 6:
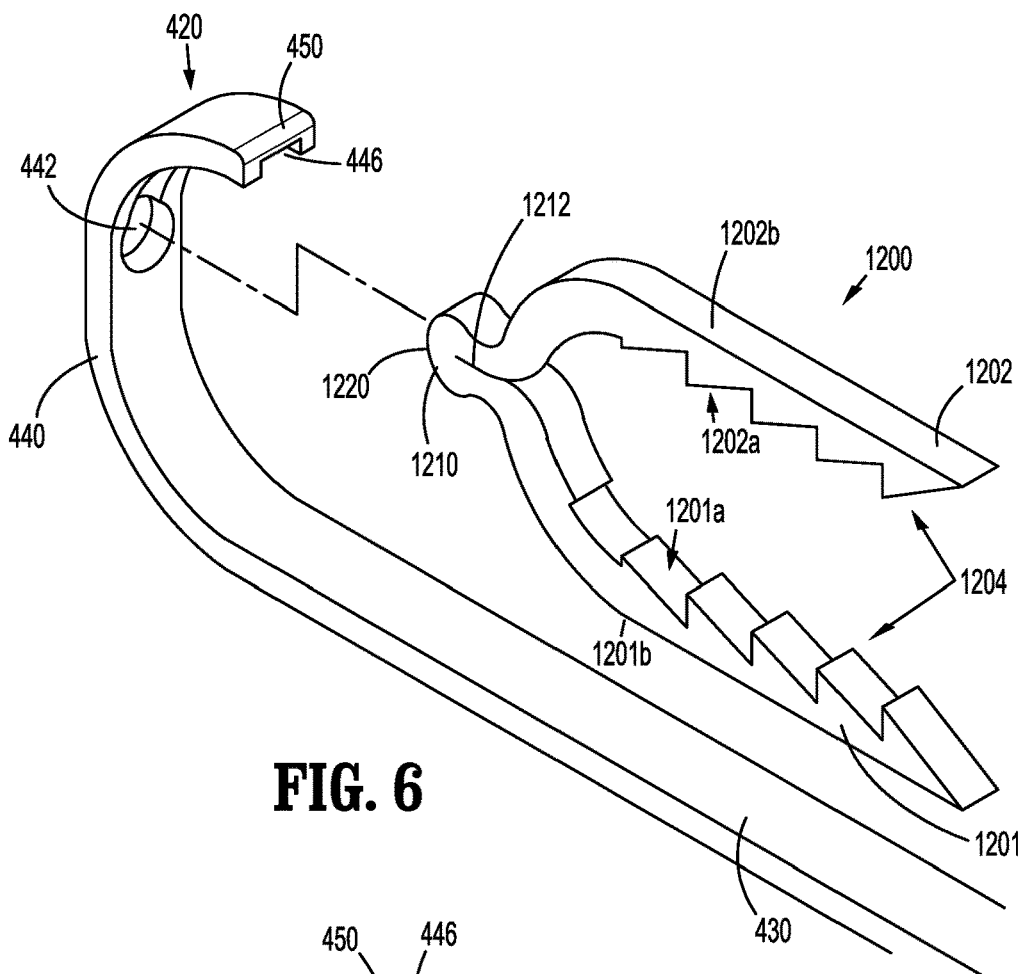
FIG. 6 is a perspective, exploded view of a portion of the two-part fastener and a portion of the end effector of the surgical clip applier of FIG. 1.
Figure 7:
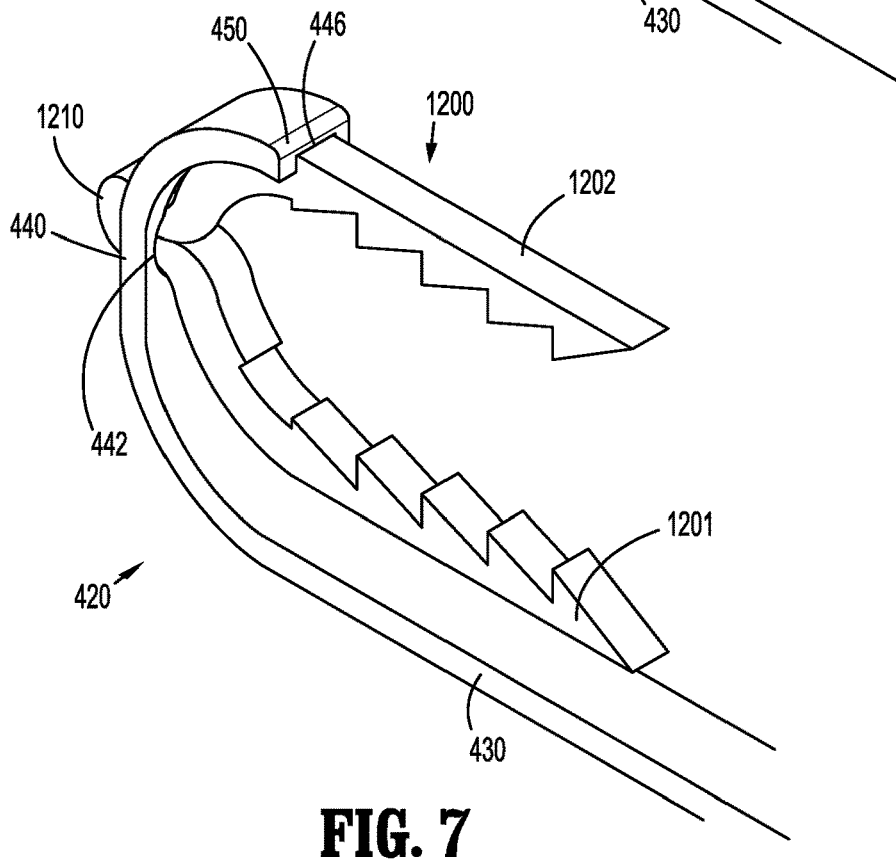
FIG. 7 is a perspective view of a portion of the two-part fastener engaged with a portion of the end effector of the surgical clip applier of FIG. 1.
Figure 8:
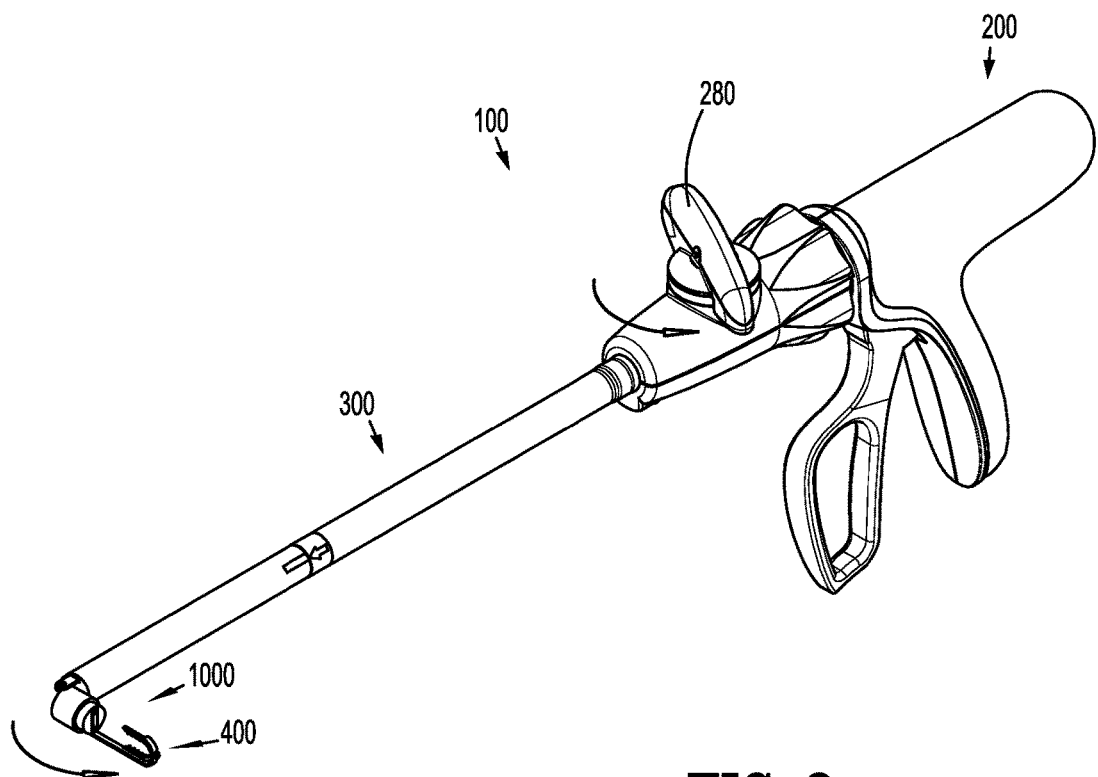
FIGS. 8 and 9 are perspective views of the surgical clip applier of FIG. 1 illustrating the end effector in various positions relative to an elongated portion of the surgical clip applier.
Figure 9:
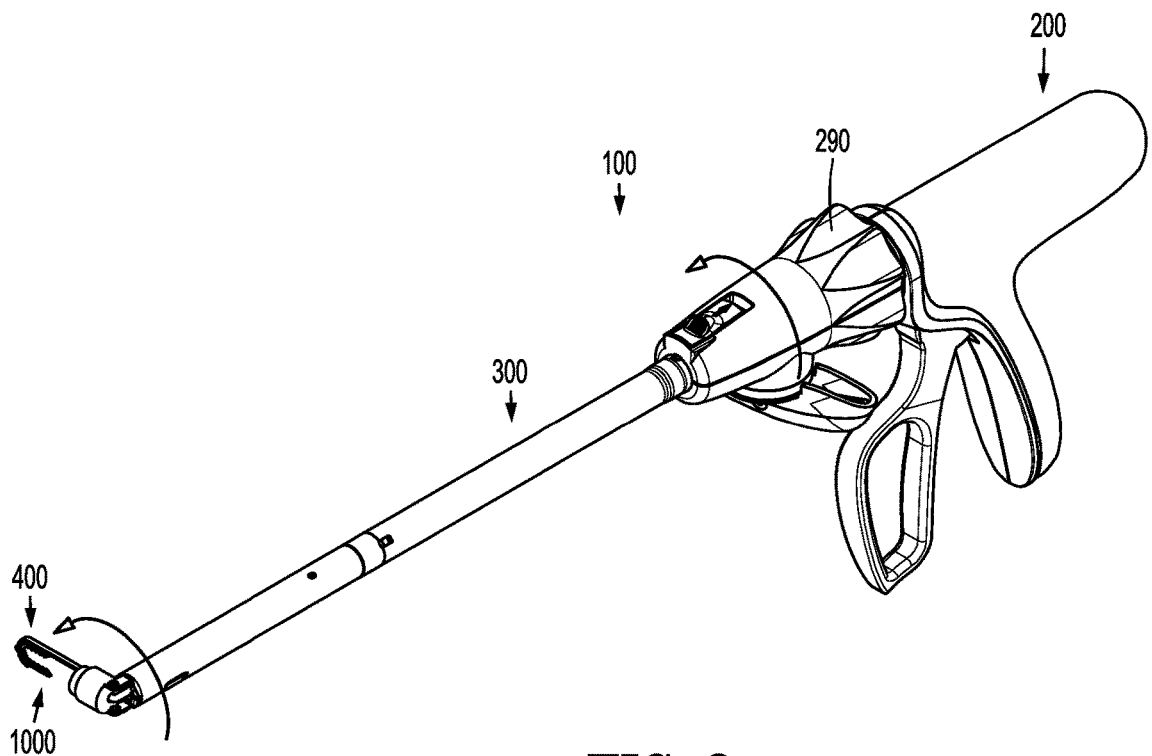
Figure 10:
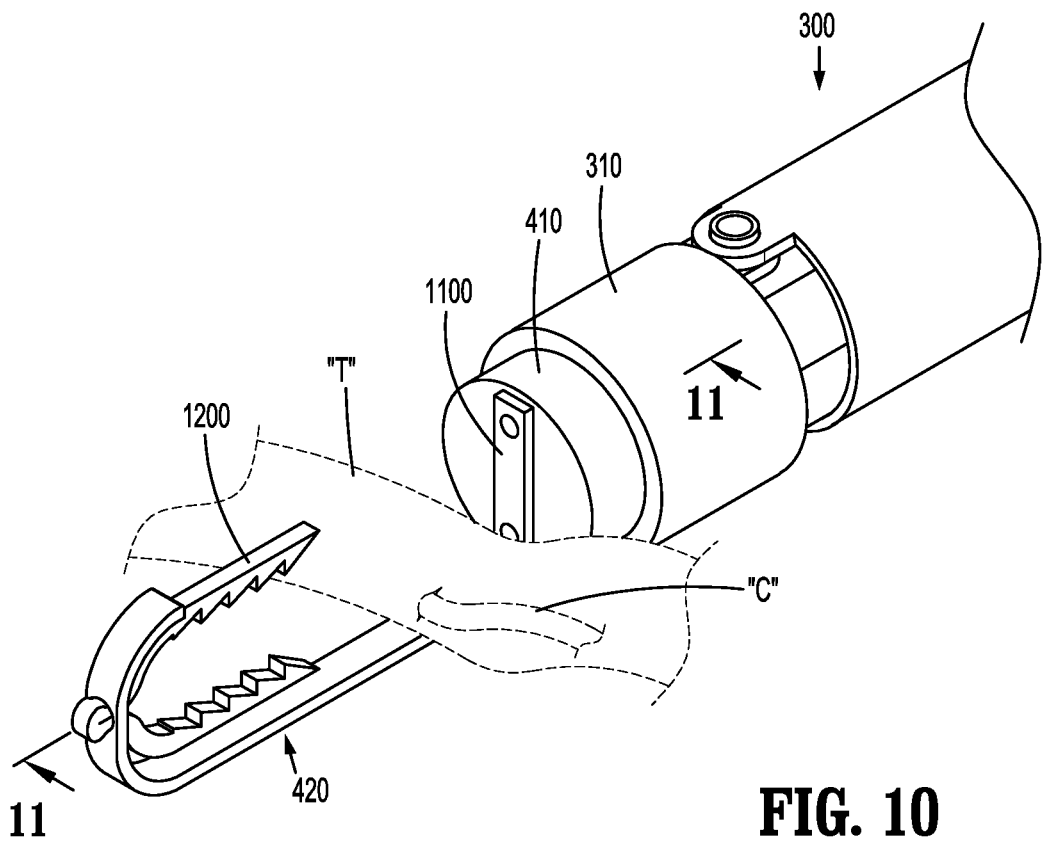
FIG. 10 is a perspective view of the two-part fastener engaged with the end effector of the surgical clip applier of FIG. 1 illustrating tissue and a catheter positioned between the two parts of the two-part fastener.
Figure 11:
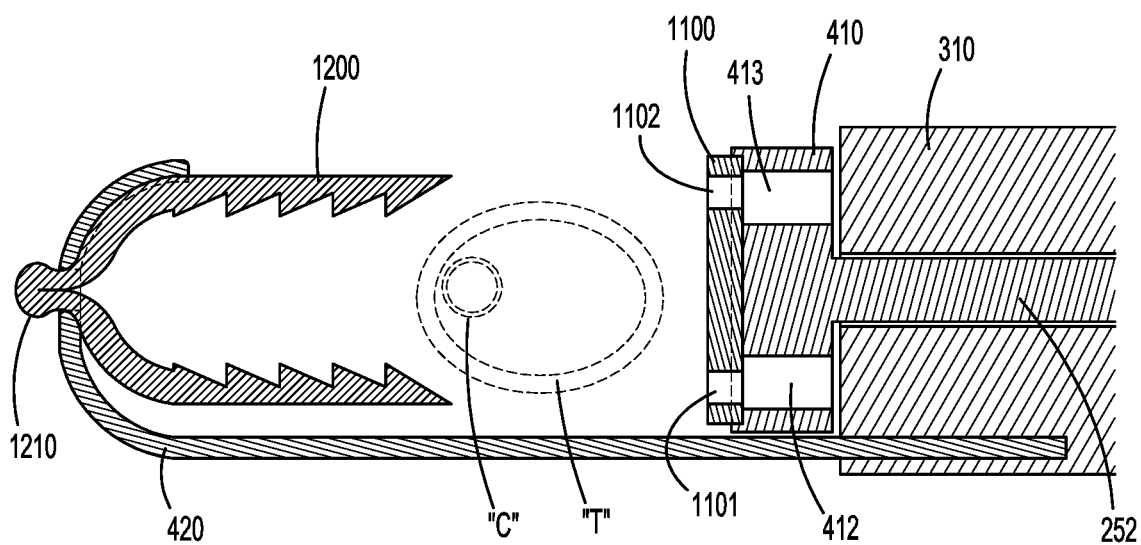
FIG. 11 is a cross-sectional view of the two-part fastener, end effector of the surgical clip applier, tissue and a catheter taken along line 11-11 in FIG. 10.
Figure 12:
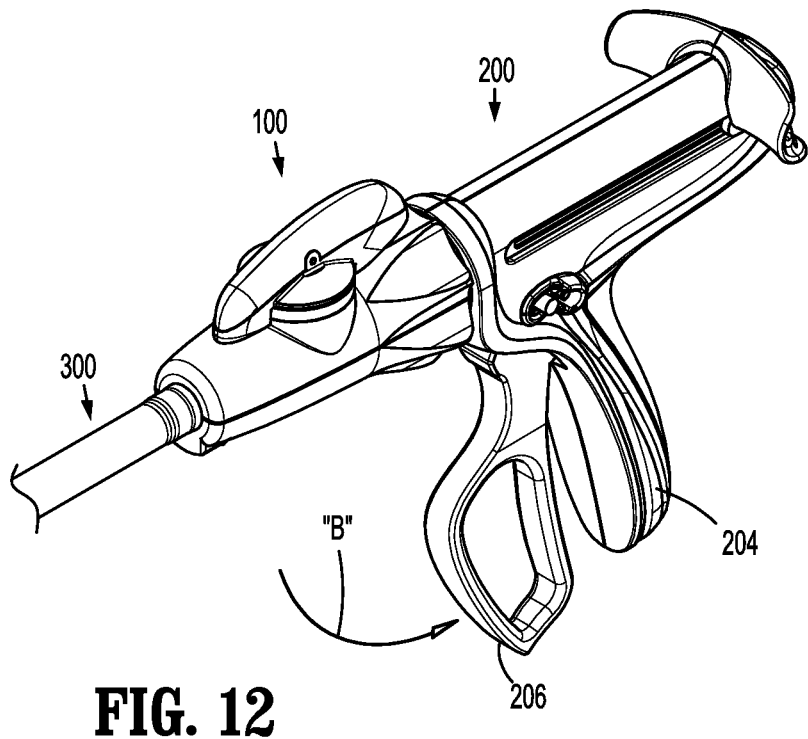
FIG. 12 is a perspective view of a proximal portion of the surgical clip applier of FIG. 1 illustrating a pivotable handle in a partially-actuated position.

In the illustrated embodiment, an inner-facing surface 1201a of the first leg 1201 and an inner-facing surface 1202a of the second leg 1202 include the plurality of teeth 1204 (see FIG. 6). However, it is also envisioned and within the scope of this disclosure that an outer-facing surface 1201b of the first leg 1201 and/or an outer-facing surface 1202b of the second leg 1202 includes the plurality of teeth 1204.

As shown in FIGS. 4-6, for example, the distal tip 1210 of the clip 1200 protrudes distally from distal ends of the first leg 1201 and the second leg 1202, and generally extends parallel to the longitudinal axis "A-A." As noted above, at least a portion of the distal tip 1210 is configured to extend through the aperture 442 defined within the C-shaped portion 440 of the distal housing 420 of the end effector 400. Additionally, a slit 1212 extends longitudinally through a portion of the distal tip 1210. As shown in FIG. 4, the slit 1212 extends distally beyond the distal housing 420 of the end effector 400 when the clip 1200 is engaged with the distal housing 420. Further, the slit 1212 does not extend to a distal-most end 1220 of the clip 1200 (FIG. 6). In use, as discussed in further detail below, when a user wants to remove the two-part fastener 1000 from securement on tissue, for instance, the user can cut the distal tip 1210 of the clip 1200 (e.g., from a location at or adjacent the distal-most end 1220 of the clip 1200 to the slit 1212) to separate the first leg 1201 of the clip 1200 from the second leg 1202 of the clip 1200, thereby facilitating removal of the two-part fastener 1000 from tissue.

Referring now to FIGS. 8-19, when a user desires to place the two-part fastener 1000 onto a vessel or tissue "T" and/or a catheter "C," for instance, (e.g., to variably occlude a vessel, or to retain a catheter in a vessel without occluding the vessel such as during cholangiograms), the user initially engages the base 1100 of the two-part fastener 1000 with the collar 410 of the end effector 400, and engages the clip 1200 of the two-part fastener 1000 with the distal housing 420 of the end effector 400. Alternatively, the user ensures the two-part fastener 1000 is properly engaged with the end effector 400. Next, the user can position the end effector 400 at a desired location by articulating the end effector 400 by actuating an articulation knob 280 (FIG. 8) and/or by rotating the end effector 400 by actuating a rotation knob 290 (FIG. 9), for instance.

After the end effector 400 is in its desired position (e.g., FIG. 10), the collar 410 of the end effector 400 is moved distally relative to the distal housing 420 of the end effector 400 by actuating the pivotable handle 206 in the general direction of arrow "B" (FIG. 12), or another actuation mechanism, thereby advancing the drive shaft 252 distally, which moves the base 1100 toward the clip 1200 of the two-part fastener 1000. (Other structures for moving the collar 410 relative to the distal housing 420, such as depressing a button, are also envisioned.) When the base 1100 moves a sufficient distance relative to the clip 1200, the first aperture 1101 of the base 1100 surrounds or engages a proximal portion of the first leg 1201 of the clip 1200, and the second aperture 1102 of the base 1100 surrounds or engages a proximal portion of the second leg 1202 of the clip 1200.

Figure 13:
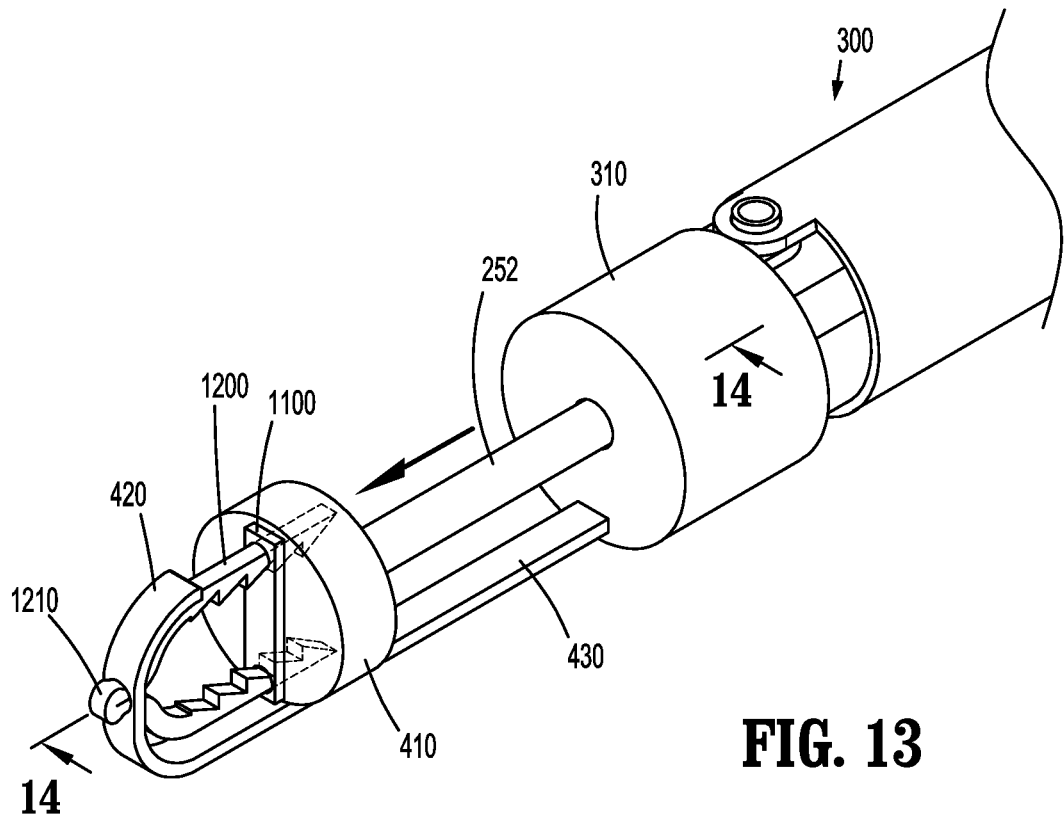
FIG. 13 is a perspective view of a distal portion of the surgical clip applier of FIG. 1 corresponding to the pivotable handle being in the partially-actuated position of FIG. 12.
Figure 14:
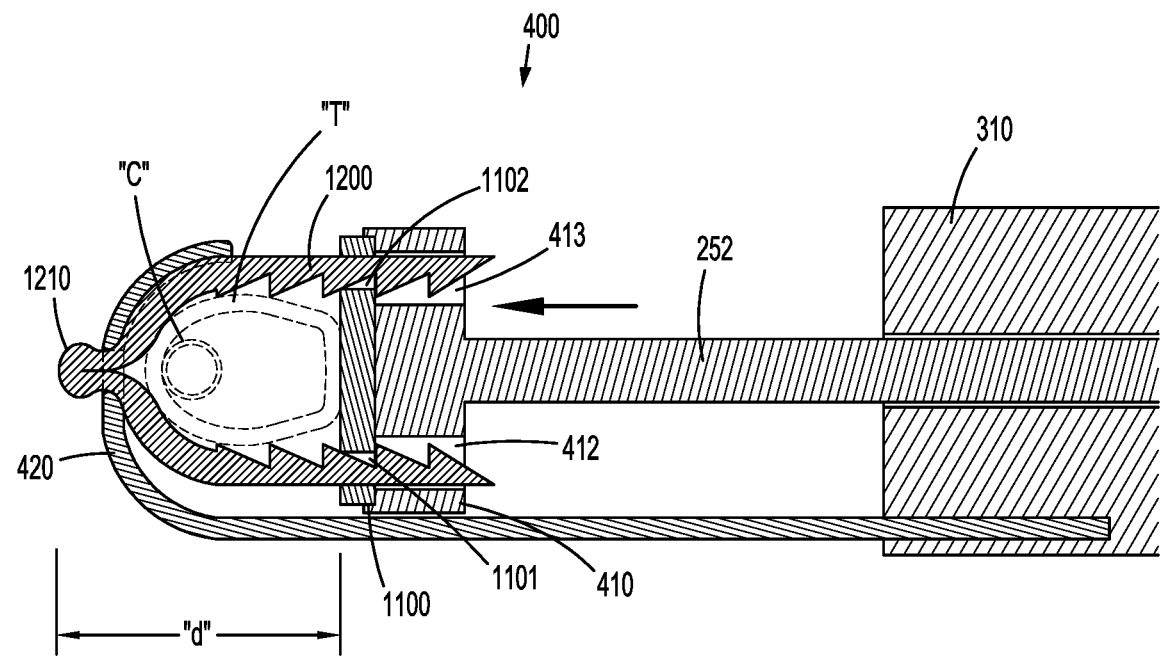
FIG. 14 is a cross-sectional view of the two-part fastener and end effector of the surgical clip applier taken along line 14-14 in FIG. 13, and further illustrating tissue and the catheter positioned between the two parts of the two-part fastener.
Figure 15:
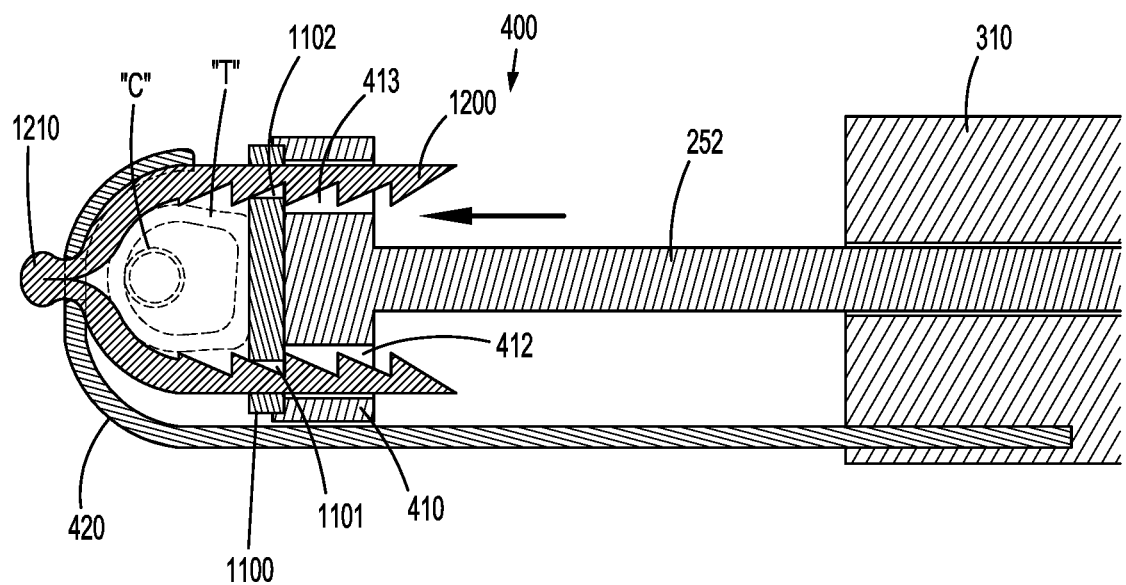
FIG. 15 is a cross-sectional view of the two-part fastener, end effector of the surgical clip applier of FIG. 1, tissue and the catheter positioned between the two parts of the two-part fastener, and corresponding to the pivotable handle of the surgical clip applier being in a further-actuated position.

With reference to FIGS. 13-15, the collar 410 of the end effector 400 is moved closer to the distal housing 420 until a desired compression or degree of crimp of the tissue "T" and/or the catheter "C" between the base 1100 and the clip 1200 of the two-part fastener 1000 is achieved. FIG. 14 illustrates the base 1100 in a first discrete position relative to the clip 1200, and FIG. 15 illustrates the base 1100 in a second discrete position relative to the clip 1200. There are several discrete positions of the base 1100 relative to the clip 1200 that allow the catheter "C" to be fixed to the tissue "T" without occluding the vessel.

Figure 16:
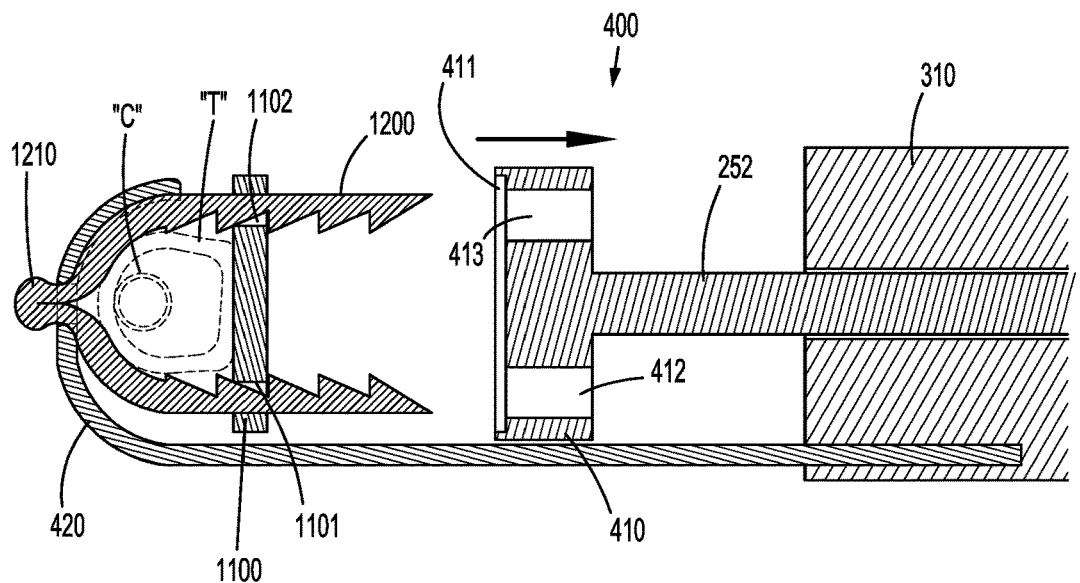
FIG. 16 is a cross-sectional view of the two-part fastener, end effector of the surgical clip applier of FIG. 1, tissue and the catheter secured between the two parts of the two-part fastener, following retraction of a collar of the surgical clip applier.
Figure 17:
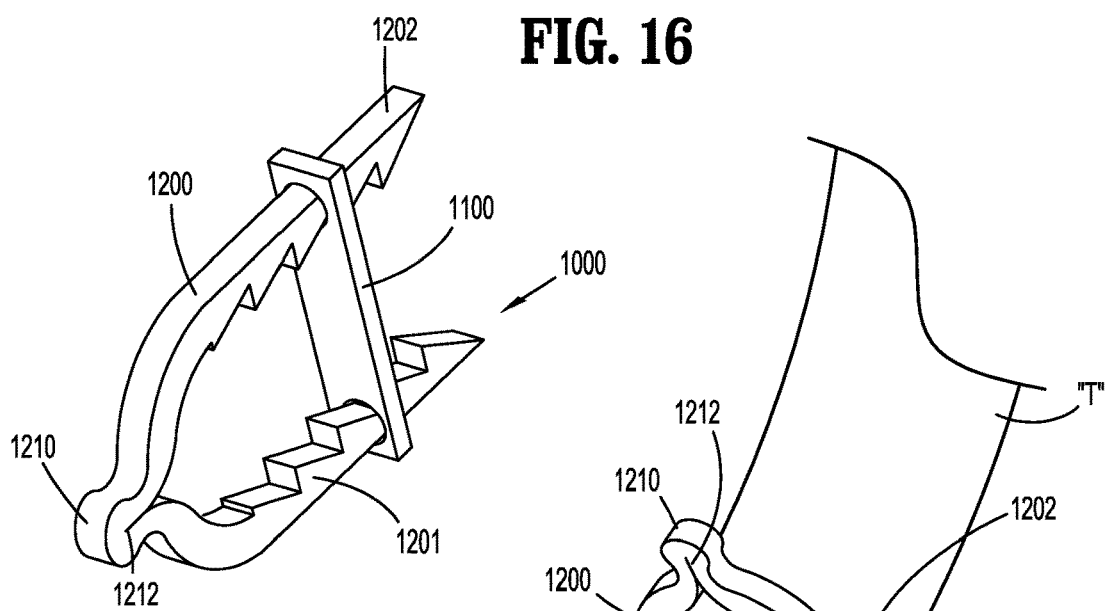
FIG. 17 is a perspective view of the two-part fastener of FIG. 1 illustrated in an engaged orientation.
Figure 18:
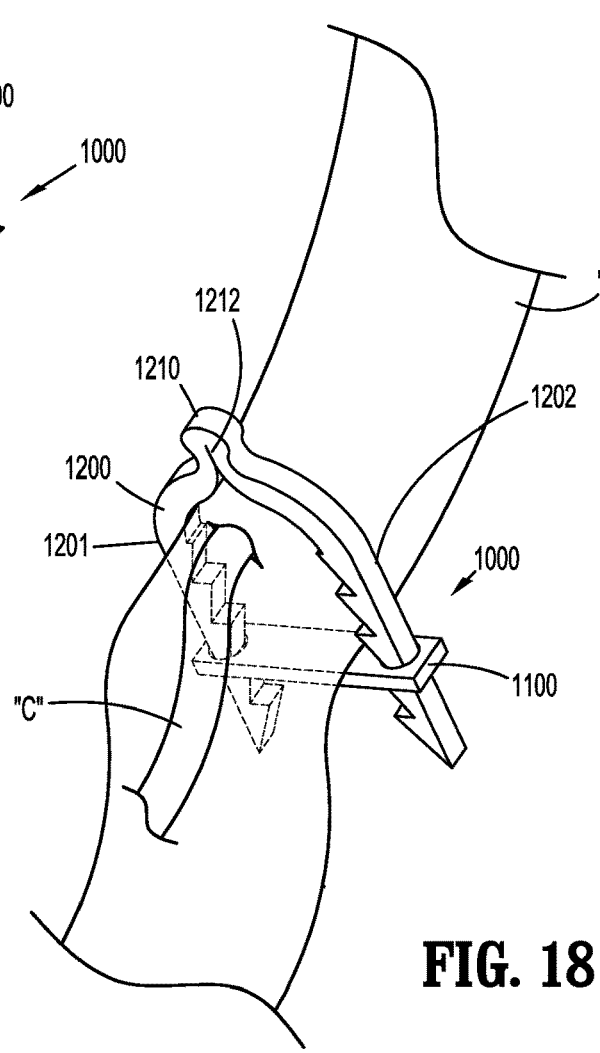
FIG. 18 is a perspective view of the two-part fastener of FIG. 1 illustrated in an engaged orientation and surrounding tissue and the catheter.
Figure 19:
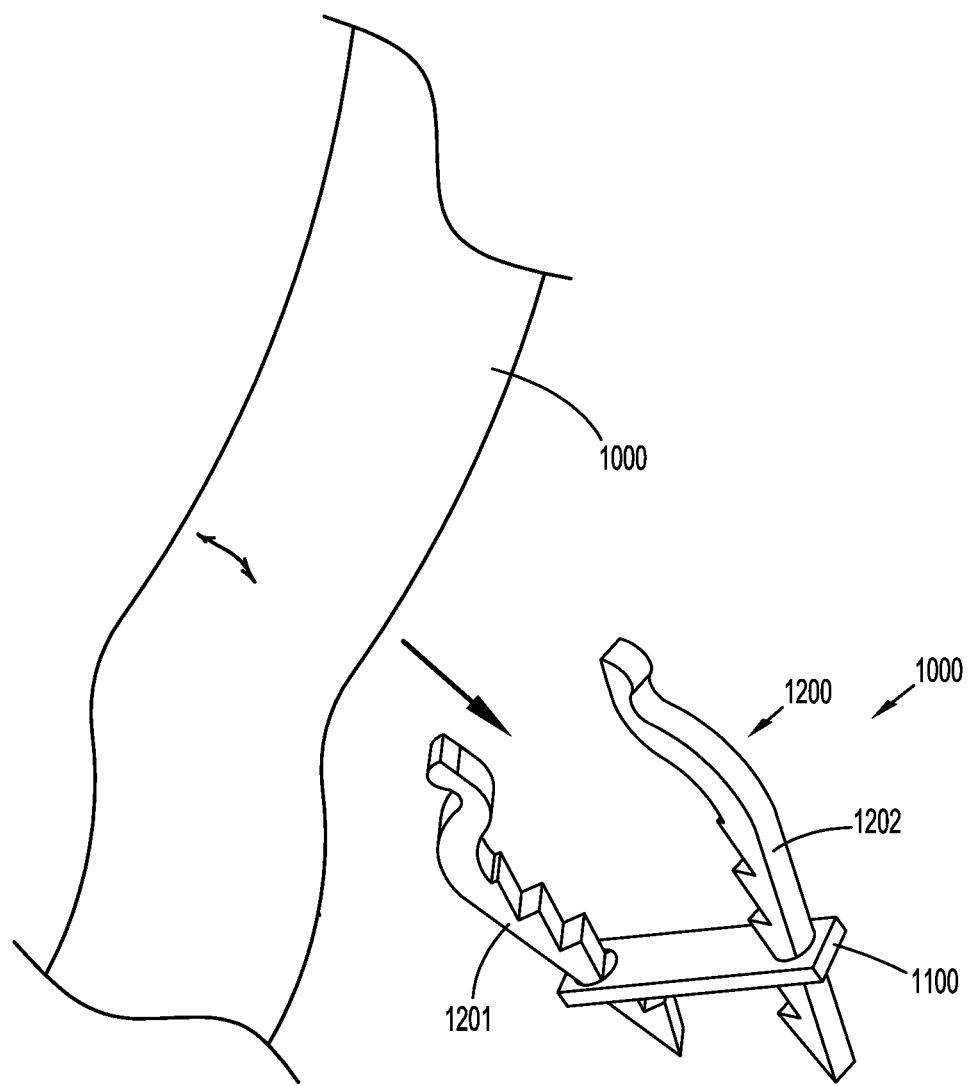
FIG. 19 is a perspective view of the two-part fastener of FIG. 1 after the two-part fastener has been cut and released from tissue and the catheter.

Referring now to FIG. 16, after the two-part fastener 1000 is desirably placed on the tissue "T" and/or the catheter "C," the drive shaft 252 is moved proximally (e.g., by moving the pivotable handle 206 away from the stationary handle 204), thereby retracting the collar 410 of the end effector 400 relative to the distal housing 420. As shown, the base 1100 remains engaged with the clip 1200 of the two-part fastener 1000. Additionally, moving the surgical clip applier 100 distally relative to the tissue "T" causes the distal housing 420 of the end effector 400 to move out of engagement with the distal tip 1210 of the clip 1200 of the two-part fastener 1000, thereby leaving the two-part fastener 1000 secured to the tissue "T" and/or the catheter "C" (FIG. 18).

After the surgical clip applier 100 is removed, a surgical procedure, such as a cholangiogram, may be performed. When the surgical procedure is complete, for instance, the two-part fastener 1000 may be removed from the tissue "T" and/or the catheter "C." To remove the two-part fastener 1000, the user may cut or sufficiently clamp the distal tip 1210 of the clip 1200, e.g., adjacent the slit 1212, to separate the first leg 1201 of the clip 1200 from the second leg 1202 of the clip 1200 (see FIG. 19). After the first leg 1201 of the clip 1200 and the second leg 1202 of the clip 1200 have been separated, the two-part fastener 1000 can easily be removed from a body cavity, for instance (e.g., using graspers).

The present disclosure also includes a surgical clip-applying system, which includes both the surgical clip applier 100 and the two-part fastener 1000. Additionally, the present disclosure includes methods of installing and/or removing the two-part fastener 1000, and methods of fixing a catheter to a vessel using the surgical clip applier 100 and the two-part fastener 1000.

The various embodiments disclosed herein may also be configured to work with robotic surgical systems and what is commonly referred to as "Telesurgery." Such systems employ various robotic elements to assist the surgeon in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 20:
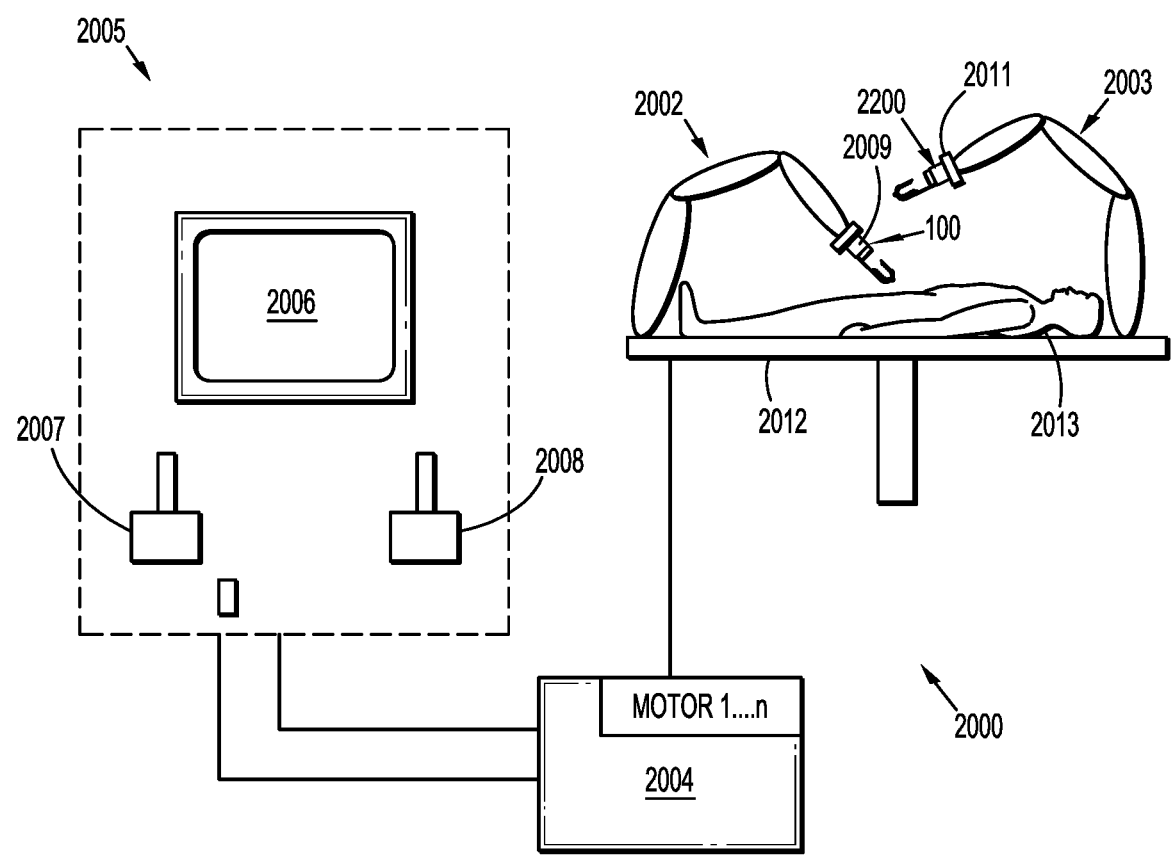
FIG. 20 is a schematic illustration of a robotic surgical system configured for use in accordance with the disclosure.

With reference to FIG. 20, a surgical system, such as, for example, a robotic surgical system is shown generally as surgical system 2000 and is usable with the surgical clip applier 100, or portions thereof, of the disclosure. Surgical system 2000 generally includes a plurality of robotic arms 2002, 2003, a control device 2004, and an operating console 2005 coupled with control device 2004. Operating console 2005 includes a display device 2006, which is set up in particular to display three-dimensional images; and manual input devices 2007, 2008, by means of which a person (not shown), for example a surgeon, is able to telemanipulate robotic arms 2002, 2003 in a first operating mode, as known in principle to a person skilled in the art.

Each of the robotic arms 2002, 2003 is composed of a plurality of members, which are connected through joints. System 2000 also includes an instrument drive unit 2200 connected to distal ends of each of robotic arms 2002, 2003. The surgical clip applier 100, or portions thereof, may be attached to the instrument drive unit 2200, in accordance with any one of several embodiments disclosed herein, as will be described in greater detail below.

Robotic arms 2002, 2003 may be driven by electric drives (not shown) that are connected to control device 2004. Control device 2004 (e.g., a computer) is set up to activate the drives, in particular by means of a computer program, in such a way that robotic arms 2002, 2003, their instrument drive units 2200 and thus the surgical clip applier 100 (including the end-effector 400) execute a desired movement according to a movement defined by means of manual input devices 2007, 2008. Control device 2004 may also be set up in such a way that it regulates the movement of robotic arms 2002, 2003 and/or of the drives.

Surgical system 2000 is configured for use on a patient 2013 lying on a patient table 2012 to be treated in a minimally invasive manner by means of the surgical clip applier 100. Surgical system 2000 may also include more than two robotic arms 2002, 2003, the additional robotic arms likewise being connected to control device 2004 and being telemanipulatable by means of operating console 2005.

Reference may be made to U.S. Pat. No. 8,828,023, entitled "Medical Workstation," the entire content of which is incorporated herein by reference, for a detailed discussion of the construction and operation of surgical system 2000.

It should be understood that the foregoing description is only illustrative of the disclosure. Various alternatives and modifications can be devised by those skilled in the art without departing from the disclosure. Accordingly, this disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical clip applier, comprising:
an elongated portion defining a longitudinal axis and including a distal end;
a drive shaft extending at least partially through the elongated portion;
an end effector disposed adjacent the distal end of the elongated portion, the end effector including a collar and a distal housing, the collar coupled to the drive shaft and movable relative to the distal housing, and
a two-part fastener supported by the end effector,
wherein the collar is configured to support a base of the two-part fastener, the distal housing including a leg and a C-shaped portion extending from a distal end of the leg, the C-shaped portion of the distal housing configured to support a clip of the two-part fastener such that a first leg and a second leg of the clip extend in a proximal direction toward the base,
wherein the collar of the end effector defines a first leg aperture and a second leg aperture, the first leg aperture configured to allow a first leg of the clip of the two-part fastener to extend through the collar, the second leg aperture configured to allow a second leg of the clip of the two-part fastener to extend through the collar, and
wherein the base of the two-part fastener defines a first leg aperture of the base and a second leg aperture of the base, the first leg aperture of the base configured to allow the first leg of the clip of the two-part fastener to extend through the base, the second leg aperture of the base configured to allow the second leg of the clip of the two-part fastener to extend through the base.

2. The surgical clip applier according to claim 1, wherein a distal-most end of the C-shaped portion of the distal housing defines an aperture.

3. The surgical clip applier according to claim 2, wherein the C-shaped portion of the distal housing defines a slot extending laterally from the aperture, the slot configured to support a portion of the clip of the two-part fastener.

4. The surgical clip applier according to claim 1, wherein the distal housing is fixed from longitudinal movement relative to the elongated portion.

5. The surgical clip applier according to claim 1, wherein the collar of the end effector defines a recess for accepting the base of the two-part fastener partially in the recess.

6. The surgical clip applier according to claim 5, wherein the first leg aperture of the collar is defined within the recess of the collar and the second leg aperture of the collar is defined within the recess of the collar.

7. The surgical clip applier of claim 1, wherein each of the first leg and the second leg of the clip of the two-part fastener includes a plurality of teeth configured to engage the base of the two-part fastener in a ratcheting manner when the first and second legs pass through the first and second leg apertures of the base.

8. The surgical clip applier of claim 1, wherein the collar is configured such that upon distal advancement of the drive shaft toward the end effector, the first leg of the clip extends through the first leg aperture of the collar and an aligned first aperture in the base, and the second leg of the clip extends through the second leg aperture of the collar and an aligned second aperture in the base.

9. A surgical clip-applying system, comprising:
a surgical clip applier, including:

an elongated portion defining a longitudinal axis and including a distal end; and an end effector disposed adjacent the distal end of the elongated portion, the end effector including a collar and a distal housing, at least one of the collar or the distal housing being movable along the longitudinal axis relative to the elongated portion; and a two-part fastener, including:

a base configured to be supported by the collar of the end effector of the surgical clip applier; and a clip configured to be supported by the distal housing of the end effector of the surgical clip applier, and including a first leg and a second leg, the first leg and the second leg each extending in a proximal direction from the distal housing toward the base, wherein a predetermined amount movement of at least one of the collar or the distal housing relative to the elongated portion causes the base of the two-part fastener to engage the clip of the two-part fastener, wherein the collar of the end effector defines a first leg aperture and a second leg aperture, and the base of the two-part fastener defines a first leg aperture and a second leg aperture, and wherein after a predetermined amount of movement of the at least one of the collar or the distal housing relative to the elongated portion, the first leg of the clip of the two-part fastener extends through the first leg aperture of the collar and through the first leg aperture of the base of the two-part fastener, and the second leg of the clip of the two-part fastener extends through the second leg aperture of the collar and through the second leg aperture of the base of the two-part fastener.

10. The surgical clip-applying system according to claim 9, wherein the distal housing of the end effector includes a C-shaped portion.

11. The surgical clip-applying system according to claim 9, wherein the base of the two-part fastener defines a first aperture and a second aperture.

12. The surgical clip-applying system according to claim 11, wherein the clip of the two-part fastener is C-shaped and includes a first leg and a second leg, the first leg configured to selectively extend through the first aperture of the base of the two-part fastener, and the second leg configured to selectively extend through the second aperture of the base of the two-part fastener.

13. The surgical clip-applying system according to claim 12, wherein each of the first leg and the second leg of the clip of the two-part fastener includes a plurality of teeth configured to engage the base of the two-part fastener in a ratcheting manner.

14. The surgical clip-applying system according to claim 9, wherein a distal-most end of the distal housing of the end effector defines an aperture.

15. The surgical clip-applying system according to claim 14, wherein a distal end of the clip of the two-part fastener includes a distal tip configured to selectively extend through the aperture of the distal housing of the end effector.

16. The surgical clip-applying system according to claim 9, wherein the base of the two-part fastener is supported partially within a recess of the collar of the end effector.

17. A surgical clip-applying system, comprising:

a surgical clip applier, including:

an elongated portion defining a longitudinal axis and including a distal end; and an end effector disposed adjacent the distal end of the elongated portion, the end effector including a collar and a distal housing, at least one of the collar or the distal housing being movable along the longitudinal axis relative to the elongated portion; and a two-part fastener, including:

a base configured to be supported by the collar of the end effector of the surgical clip applier; and a clip configured to be supported by the distal housing of the end effector of the surgical clip applier, and including a first leg and a second leg, wherein a predetermined amount movement of at least one of the collar or the distal housing relative to the elongated portion causes the base of the two-part fastener to engage the clip of the two-part fastener, wherein a distal-most end of the distal housing of the end effector defines an aperture, wherein a distal end of the clip of the two-part fastener includes a distal tip configured to selectively extend through the aperture of the distal housing of the end effector, and wherein the distal tip of the clip of the two-part fastener defines a slit extending generally parallel to the first leg of the clip of the two-part fastener.

18. The surgical clip-applying system according to claim 17, wherein when the distal tip of the clip of the two-part fastener extends through the aperture of the distal housing of the end effector, and the slit of the distal tip extends distally beyond the distal-most end of the distal housing of the end effector.

* * * * *